US010487138B2

(12) United States Patent
Felföldi et al.

(10) Patent No.: US 10,487,138 B2
(45) Date of Patent: Nov. 26, 2019

(54) IMMUNOGLOBULIN PURIFICATION USING PRE-CLEANING STEPS

(71) Applicant: RICHTER GEDEON NYRT., Budapest (HU)

(72) Inventors: Ferenc Felföldi, Budapest (HU); Zsuzsa Benkö, Budapest (HU); Melinda Gáspár, Budapest (HU)

(73) Assignee: RICHTER GEDEON NYRT., Budapest (HU)

( * ) Notice: Subject to any disclaimer, the term of this patent is extended or adjusted under 35 U.S.C. 154(b) by 364 days.

(21) Appl. No.: 15/120,359

(22) PCT Filed: Mar. 9, 2015

(86) PCT No.: PCT/EP2015/054862
§ 371 (c)(1),
(2) Date: Aug. 19, 2016

(87) PCT Pub. No.: WO2015/135884
PCT Pub. Date: Sep. 17, 2015

(65) Prior Publication Data
US 2017/0058019 A1 Mar. 2, 2017

(30) Foreign Application Priority Data

Mar. 10, 2014 (HU) ..................................... 1400131
Feb. 9, 2015 (HU) ..................................... 1500053

(51) Int. Cl.
*B01J 41/20* (2006.01)
*C07K 1/22* (2006.01)
*C07K 1/16* (2006.01)
*C07K 1/36* (2006.01)
*C07K 16/06* (2006.01)
*C07K 1/18* (2006.01)
*C07K 16/28* (2006.01)
*B01J 39/26* (2006.01)
*C07K 16/24* (2006.01)

(52) U.S. Cl.
CPC ............ *C07K 16/065* (2013.01); *B01J 39/26* (2013.01); *B01J 41/20* (2013.01); *C07K 1/165* (2013.01); *C07K 1/18* (2013.01); *C07K 1/22* (2013.01); *C07K 1/36* (2013.01); *C07K 16/241* (2013.01); *C07K 16/2887* (2013.01)

(58) Field of Classification Search
None
See application file for complete search history.

(56) References Cited

U.S. PATENT DOCUMENTS 5,429,746 A * 7/1995 Shadle ............... B01D 15/327
210/635
2003/0040027 A1 * 2/2003 Ritter ............... G01N 33/54373
435/7.21
2006/0257972 A1 11/2006 Ishihara
2007/0037734 A1 * 2/2007 Rossi ................. C07K 14/7155
530/350
2011/0065901 A1 * 3/2011 Soice ..................... C07K 16/00
530/388.1
2011/0251374 A1 10/2011 Suenaga et al.
2012/0177640 A1 * 7/2012 Burg ........................ C07K 1/18
424/133.1
2012/0264920 A1 * 10/2012 Wang .................... B01D 15/125
530/388.1
2013/0041139 A1 * 2/2013 Brown ..................... C07K 1/22
530/388.1
2013/0183315 A1 * 7/2013 Attinger ............. A61K 39/3955
424/139.1

FOREIGN PATENT DOCUMENTS

| EP | 0 299 746 A1 | 1/1989 |
| EP | 0 345 549 A2 | 12/1989 |
| EP | 0 550 400 A2 | 7/1993 |
| WO | WO 91/18975 A1 | 12/1991 |
| WO | WO 92/16553 | 10/1992 |
| WO | WO 92/22653 | 12/1992 |
| WO | WO 94/11026 | 5/1994 |
| WO | WO 95/22389 | 8/1995 |
| WO | WO 97/29131 | 8/1997 |
| WO | WO 98/45331 | 10/1998 |
| WO | WO 03/002713 A2 | 1/2003 |
| WO | WO 03/041859 A1 | 5/2003 |
| WO | WO 03/102132 A2 | 12/2003 |

(Continued)

OTHER PUBLICATIONS

Office Action corresponding to Japanese Patent Application Serial No. G8029WOJP dated Sep. 26, 2017.
International Search Report and Written Opinion of the International Searching Authority for International Application No. PCT/EP2015/054862 (dated May 13, 2015).
Gagnon, "Technology trends in antibody purification," Journal of Chromatography A, 1221, pp. 57-70 (2012).
Liu et al., "Recovery and purification process development for monoclonal antibody production," mAbs 2:5, Landes Bioscience, pp. 480-499 (Sep./Oct. 2010).

(Continued)

*Primary Examiner* — Daniel E Kolker
*Assistant Examiner* — James L Rogers
(74) *Attorney, Agent, or Firm* — Jenkins, Wilson, Taylor & Hunt, P.A.

(57) ABSTRACT

The present invention relates to the purification of immunoglobulins and the problem of providing a method for purifying an immunoglobulin in an efficient and cost-effective manner and with satisfactory purity and yield. In particular, the present invention addresses the aspect of the re-use of the rather cost-intensive chromatography materials, in particular the lifetime of the chromatography materials used in the capture step of the downstream process, and how this can be increased while reducing the technical complexity of the purification process.

5 Claims, 5 Drawing Sheets

(56) References Cited

FOREIGN PATENT DOCUMENTS

| | | | |
|---|---|---|---|
| WO | WO 2004/076485 A1 | 9/2004 | |
| WO | WO 2004/087761 A1 | 10/2004 | |
| WO | WO 2005/016968 A2 | 2/2005 | |
| WO | WO 2005/082483 A1 | 9/2005 | |
| WO | WO 2006/024497 A1 | 3/2006 | |
| WO | WO 2009/058812 A1 | 5/2009 | |
| WO | WO 2009/138484 A2 | 11/2009 | |
| WO | WO 2010/071208 A1 | 6/2010 | |
| WO | WO 2010/141039 A1 | 12/2010 | |
| WO | WO 2011/017514 A1 | 2/2011 | |
| WO | WO 2011/049798 A1 | 4/2011 | |
| WO | WO 2011/090720 A2 | 7/2011 | |
| WO | WO 2011/150110 A1 | 12/2011 | |
| WO | WO 2013/066707 A1 | 5/2013 | |
| WO | WO 2013/067301 A1 | 5/2013 | |
| WO | WO-2013180647 A1 * | 12/2013 | ............. C07K 16/00 |
| WO | WO 2015/135884 A1 | 9/2015 | |

OTHER PUBLICATIONS

Farid, "Economic Drivers and Trade-Offs in Antibody Purification Processes: The future of therapeutic MAbs lies in the development of economically feasible downstream processes," BioPharm International Supplements, exerpt from chapter entitled "Process Economic Drivers in Industrial Monoclonal Antibody Manufacture,"John Wiley and Sons, Process Scale Purification of Antibodies, pp. 1-9 (Oct. 2, 2009).

Kelley et al., "Downstream processing of monoclonal antibodies: current practices and future opportunities," Process Scale Purification of Antibodies, Chapter 1, John Wiley & Sons, Inc., pp. 1-23 (2009).

Luhrs et al., "Evicting hitchhiker antigens from purified antibodies," Journal of Chromatography B, 877, pp. 1543-1552 (2009).

Ishihara et al., "Accelerated purification process development of monoclonal antibodies for shortening time to clinic design and case study of chromatography processes," Journal of Chromatography A, 1176, pp. 149-156 (2007).

Yigzaw et al., "Exploitation of the Adsorptive Properties of Depth Filters for Host Cell Protein Removal during Monoclonal Antibody Purification," Biotechnol. Prog., 22, pp. 288-296 (2006).

Fahrner et al., "Industrial Purification of Pharmaceutical Antibodies: Development, Operation, and Validation of Chromatography Processes," Department of Recovery Sciences and Department of Analytical Chemistry, Biotechnology and Genetic Engineering Reviews, vol. 18, pp. 301-327 (Jul. 2001).

Gagnon, "Purification Tools for Monoclonal Antibodies," Validated Biosystems, Inc., pp. 1-252 (1996).

"Note for guidance on virus validation studies: the design, contribution and interpretation of studies validating the inactivation and removal of viruses"; EMA Committee for proprietary medical products (CPMP), CPMP/BWP/268/95, pp. 2-13 (Feb. 14, 1996).

Bulens et al., "Construction and characterization of a functional chimeric murine-human antibody directed against human fibrinfragment-D dimer," Eur. J. Biochem. 195, pp. 235-242 (1991).

Vandamme et al., "Construction and characterization of a recombinant murine monocloal antibody directed against human fibrin fragment-D dimer," Eur. J. Biochem., 192, pp. 767-775 (1990).

Fuglistaller, "Comparison of immunoglobulin binding capacities and ligand leakage using eight different protein A affinity chromatography matrices," Journal of Immunological Methods, 124, pp. 171-177 (1989).

IPRP corresponding to International Patent Application No. PCT/EP2015/054862 dated Sep. 13, 2016.

* cited by examiner

Figure 1: Process schemes of conventional purification methods for immunoglobulins
Figure 1A: Universal large scale process scheme
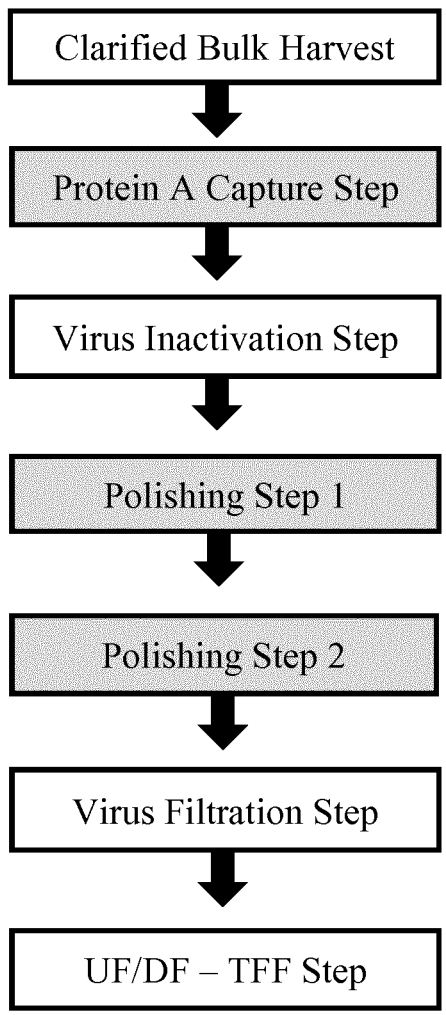

Figure 1: Process schemes of conventional purification methods for immunoglobulins
Figure 1B: Classical large scale process scheme
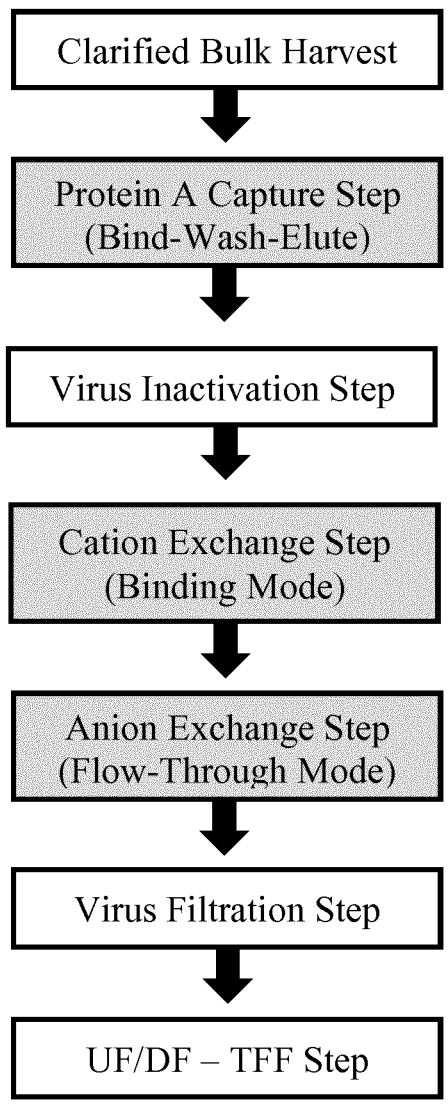

Figure 2: Exemplary process schemes of the invention using pre-cleaning steps
Figure 2A: Large scale process scheme with pre-cleaning steps and Protein A capture
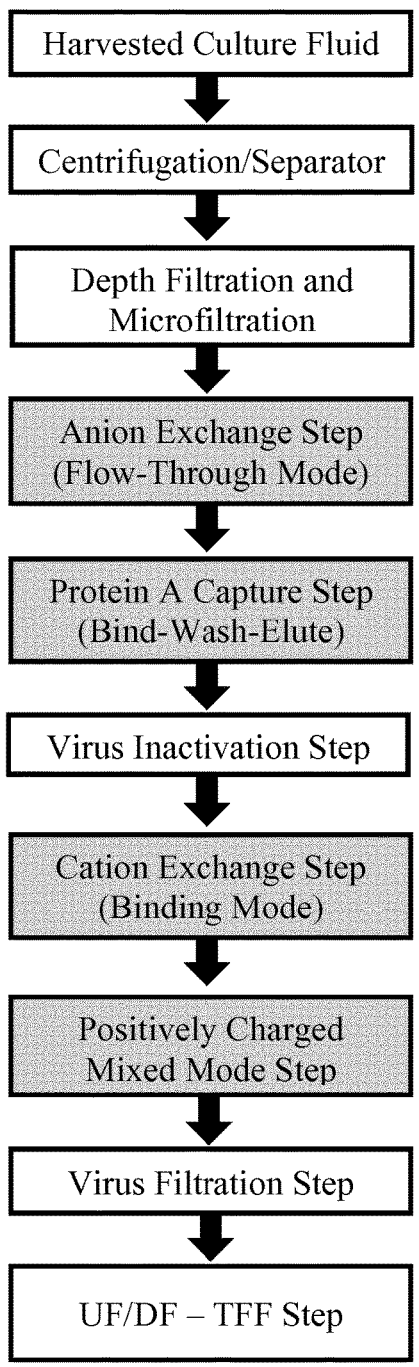

Figure 2: Exemplary process schemes of the invention using pre-cleaning steps
Figure 2B: Large scale process scheme with pre-cleaning steps, Mixed Mode capture, and an intermediate Protein A affinitychromatography
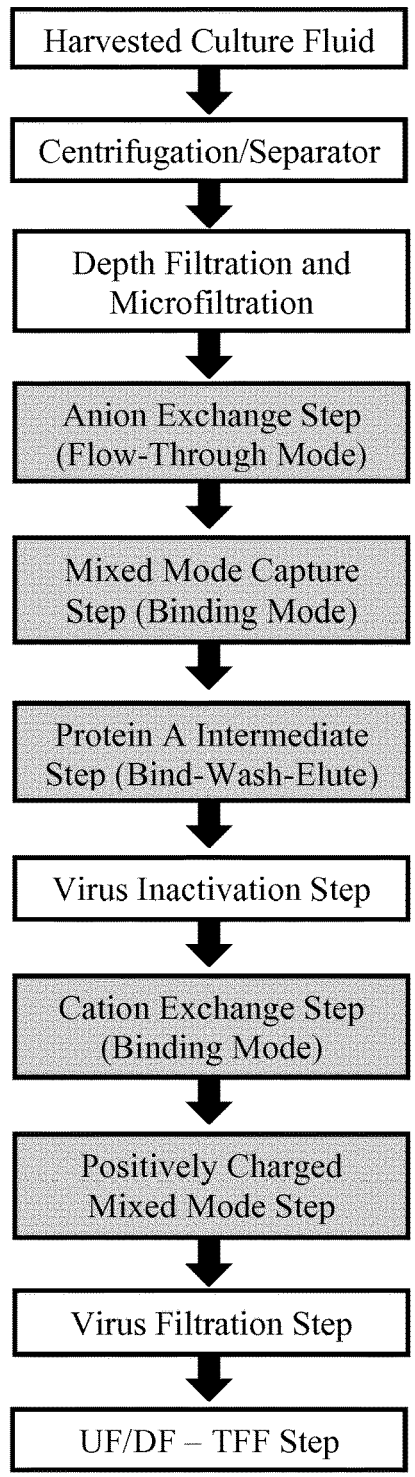

Figure 2: Exemplary process schemes of the invention using pre-cleaning steps
Figure 2C: Large scale process scheme with pre-cleaning steps, Mixed Mode capture, and without a Protein A affinity chromatography
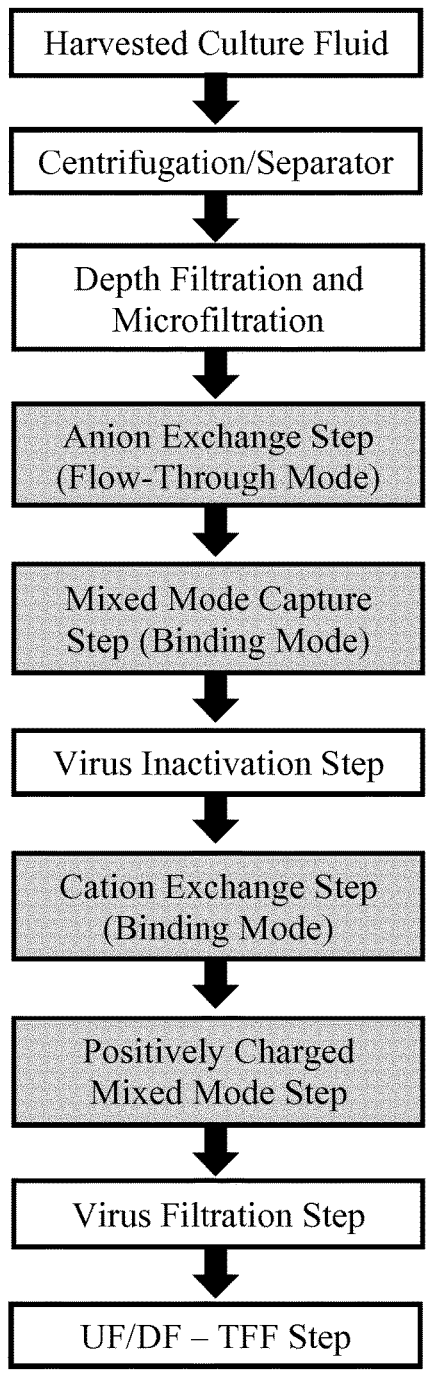

IMMUNOGLOBULIN PURIFICATION USING PRE-CLEANING STEPS

FIELD OF THE INVENTION

The present invention relates to methods of purifying antibodies from a cell culture-derived composition using pre-cleaning steps prior to a capture step and/or further polishing steps subsequent to the capture step.

BACKGROUND OF THE INVENTION

The selection of efficient and economic downstream sequences for purification of polypeptides produced by recombinant DNA technology is a crucial step in the development of every new biopharmaceutical intended for therapeutic use. In the recent past the need for large scale purification processes for monoclonal antibodies (mabs), due to their exceptionally high therapeutic dosages in medical use, has been further intensified with the use of improved cell culture methods resulting in higher cell densities and higher expression rates. The increasing concentrations in the culture fluids of product and contaminants set higher demands on the capture chromatography, on its preceding sample clarification steps and on the subsequent polishing chromatographies. The entire downstream process has to: (i) manage an increased mass of product, (ii) efficiently remove increased process- and product-related impurities to below defined acceptance criteria, and (iii) maintain economic yields and sufficient quality of the mab. Usually, the downstream process accounts for a major part of the total manufacturing costs of therapeutic antibodies.

The mabs in crude fractions are typically associated with impurities such as host cell proteins (HCP), host cell DNA, viruses, aggregates, other undesired product variants, and various leachates from process materials. The presence of these impurities is a potential health risk for patients, and hence their absence from the final product is a regulatory requirement. Only very low residual amounts will be tolerated.

The classical procedure for purifying cell-culture derived polypeptides follows the sequence of capture-intermediate-polishing chromatographies, accompanied by filtration, concentration or dialysis steps at various positions of the downstream sequence. In recent years platform approaches have been successfully established in the field of mab purification. Since mabs are a well-defined class of glycoproteins possessing common physicochemical properties, the use of a generic platform process is reasonable (Kelly B 2009). Such a universal process, with more or less product-specific adaptions, can be applied to many mabs, especially for those immunoglobulins of the same class or subclass, e.g. IgG1.

One of the most frequent capture steps used for mab purification is affinity chromatography with Protein A. This capture offers exceptional selectivity for Fc-bearing molecules, thereby removing more than 99.5% of contaminants in a single step. However, besides its advantages, two disadvantages should also be mentioned. One drawback is the undesired leaching of Protein A or fragments of Protein A which are known to be toxic (Gagnon P 1996). The other disadvantage is the high cost of this type of resin, particularly at the industrial scale necessary to purify therapeutic antibodies. A Protein A resin is approximately 30 times more expensive than an ion exchange resin. It was calculated that for the downstream processing of a 10 $m^3$ cell culture the cost for the Protein A affinity chromatography is about 4-5 million USD (Farid SS 2009).

Many solutions have been published to overcome the problem of leached Protein A (Gagnon P 1996; Fahrner R L 2001). Several approaches related to post-Protein A chromatographic steps which remove leached Protein A, such as anion exchange chromatography used in binding mode (EP0345549) or flow-through mode (WO2004076485), cation exchange chromatography (WO2009058812), hydrophobic interaction chromatography (WO9522389), or combinations of chromatographies, for instances ion exchange chromatography followed by hydrophobic interaction chromatography (WO2010141039), anion exchange chromatography followed by cation exchange chromatography (WO2011090720), or cation exchange chromatography and Mixed Mode chromatography in any order (WO2011150110). Since the required overall degree of purity for a therapeutic antibody is extremely high, a typical platform purification scheme consists of at least two post-Protein A chromatographies which are usually selected from cation exchange chromatography, anion exchange chromatography in flow-through, and hydrophobic interaction chromatography (Fahrner R L 2001, Kelly B 2009, WO9522389, WO2009138484, WO2010141039, WO2011017514, WO2011090720).

Other approaches reduce the leachates already during the Protein A affinity chromatography by using special wash steps removing leached Protein A prior to eluting the immunoglobulin. Many intermediate wash buffers were developed containing salts or additional components, for example hydrophobic electrolytes such as tetramethylammonium chloride (Fahrner R L 2001).

Some methods take effect closer to the source of the Protein A leaching by directly reducing the proteolytic activities originating from the sample. A major part of Protein A leaching is caused by proteolysis. Such reduced leaching was achieved by low temperatures and/or by adding protease inhibitors to the buffers (WO2005016968).

A special method for avoiding or reducing Protein A leaching comprises pre-treatment of the Protein A resin with surface active compounds, for example chaotropic substances such as Urea or Guandine-HCl (WO03041859).

It has been known for a long time that different types of Protein A resins display different degrees of leaching (Fuglistaller P 1989). Thus the selection of the Protein A material is an important factor. Besides the ligand itself, also the backbone matrix influences the leaching, the binding capacity, and the flow rates, (Fahrner R L 2001). These parameters taken together define the column size, the process time, and thus the economy of the affinity capture step. Moreover, during the previous decade chromatography suppliers have developed more robust Protein A ligands provided by genetic engineering of the natural *Staphylococcus aureus* Protein A sequence. These improved resins consist of a rigid matrix in combination with an improved recombinant ligand protein specially engineered to enable alkali tolerance, high binding capacity and low ligand leakage. One example is MabSelect SuRe™ from GE Healthcare Life Sciences (WO2009138484). This material can be rapidly and efficiently cleaned after the run with up to 0.5 M NaOH. However, these benefits come at a price. MabSelect SuRe and comparable modern resins are considerably more expensive than the previous Protein A resin generation. Therefore, despite these new affinity media, there is no economic benefit, rather the opposite is true. In view of the very high costs associated with Protein A-based affinity capture, it is not surprising that alternative strategies have been developed which completely avoid any use of an affinity chromatography for purification of immunoglobulins. One example is the use of high-performance tangential flow filtration in combination with non-affinity chromatographies such as anion exchange chromatography, cation exchange chromatography, hydrophobic interaction chromatography or Mixed Mode chromatography (WO03102132).

In many cases, capture steps are performed with crude input (load) materials, which can cause the contamination of (accumulation of impurities on) the affinity column resin. In absence of a proper regeneration step, this can prevent successful re-use of the capture resin. In case of the affinity capture with Protein A, it has to be emphasized that ligand leaching is not the major factor in limiting the life time of the Protein A resin. The contaminants in crude culture fluids, like lipids, oxidants, aggregates or particles, metal ions and other substances promote fouling of the resins. Besides direct effects on the Protein A binding moieties, also the matrix can be irreversibly contaminated. Reduced capacities and flow rates from run to run are the consequence. This problem is not limited to Protein A resins: fouling of chromatographic resins over their operational lifetimes is a general significant problem for commercial bioseparations. Hydrophobic ligands used for hydrophobic interaction chromatography and Mixed Mode chromatography, when used as capture steps for cell culture-derived immunoglobulins, are especially susceptible for trapping lipophilic contaminants from the culture fluids. Despite sophisticated protocols for post-run cleaning steps, the lifetime of a capture column is limited and depends on the number of cycles, the operating conditions for running and cleaning, and the purity of the sample.

Mixed Mode chromatography was described mainly as an option for a polishing step downstream to Protein A (Kelly, B. 2009, WO03102132). The use of Capto MMC in the binding mode for purification of mab is known. Special elution conditions were developed (WO2011049798). Likewise, it was shown that CaptoAdhere, preferably in the flow-through mode, is a suitable polishing step after a flow-through anion exchange chromatography performed after a Protein A affinity chromatography (WO2013066707). Furthermore, some different Mixed Mode resins were investigated in an overload and elute chromatography mode and CaptoAdhere was most preferred (WO2013067301).

To clarify the heavily contaminated culture fluids, mechanical separation steps have been employed which remove most of cell debris and aggregates. Centrifugation and filtration are the most common pre-treatment steps performed prior to load of the sample to the capture resin. For large volumes, centrifugation is performed by cell separators and the filtration steps are performed by depth filters and/or micro filters. The resulting culture fluid is then referred to as "clarified cell culture supernatant" (Liu H F 2010). Although the direct load of harvested culture fluid onto the Protein A resin is a frequent method of choice (Fahrner R L 2001), other platform technologies make use of the clarification steps, i.e. centrifugation, depth filtration, and/or microfiltration (Liu H F 2010, WO9522389, WO2001150110) in order to protect the capture column.

Pre-cleaning chromatographic steps performed alternatively or additionally to the centrifugation/filtration have only been reported sporadically. The use of immobilized metal (Zn2+) chelate chromatography (IMAC) in binding mode was used prior to Protein A on a very small scale (VanDamme A.-M. 1990, Bulens F. 1991). In contrast, weak anion exchange chromatography on DEAE Cellulose was used after centrifugation, filtration, and concentration and the obtained flow-through was then loaded onto Protein A (EP0550400). Finally, the advantages of depth filtration for pre-treatment of culture fluids prior to Protein A was investigated and compared to a less effective anion exchange chromatography on TMAE Fractogel in the flow-through mode (Yigsaw Y 2006).

SUMMARY OF THE INVENTION

The present invention relates to the purification of immunoglobulins and the problem of providing a method for purifying an immunoglobulin in an efficient and cost-effective manner and with satisfactory purity and yield. In particular, the present invention addresses the aspect of the re-use of the rather cost-intensive chromatography materials, in particular the lifetime of the chromatography materials used in the capture step of the downstream process, and how this can be increased while reducing the technical complexity of the purification process.

Conventional downstream chromatography processes for the purification of immunoglobulins from cell culture fluids usually start with a capture chromatography step in which the immunoglobulin has to be captured from a sample comprising the immunoglobulin together with impurities. The immunoglobulin is separated from the impurities largely as a result of the selective binding of the immunoglobulin to the capture chromatography resin while the impurities do not bind to the resin and are thus obtained in the flow-through, whereas the immunoglobulin is obtained in the eluate.

This capture chromatography step is usually the most expensive step in the purification of immunoglobulins, amounting to 40 to 50% of the overall downstream process costs. The capture step is particularly costly when a Protein A affinity chromatography is used. The same applies to Mixed Mode chromatography columns, which alternatively may be used as a capture chromatography step in the purification of immunoglobulins.

There is an ongoing need for cost-effective purification of immunoglobulins from large volumes of cell culture fluid and fermentation broth and from samples derived from such fluid or broth. In particular, there is a need for purification methods that are cost-effective and still efficient and satisfactory in terms of purity and yield.

It has been found that by incorporating an additional chromatography step upstream of the capture chromatography step, the overall expense of the purification process can be significantly reduced. The additional chromatography step upstream of the capture chromatography step reduces the impurity burden to which the cost-intensive capture chromatography material is exposed. This so called "pre-cleaning" step is carried out using chromatography material that is less expensive and more robust compared to the chromatography material used in the subsequent capture step and is easy to regenerate.

In order to keep the purification process as simple as possible, in a preferred embodiment the pre-cleaning step is performed in the flow-through mode, i.e. the immunoglobulin to be purified is not bound by the resin and thus obtained in the flow-through fraction, while impurities are to a large extent retained on the resin and thereby separated from the immunoglobulin.

In a further preferred embodiment, the pre-cleaning step and the capture step are connected in series, so that the flow-through of the pre-cleaning step is not temporarily stored in a collecting vessel, but is immediately passed to the capture chromatography resin.

In order to achieve the required high purity of the immunoglobulin intended for therapeutic use, the pre-cleaning step and the capture chromatography step are followed by one or more chromatographic polishing steps after the capture chromatography step.

The problem underlying the present invention is solved by the provision of a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

The invention further solves the problem of increasing viral safety in a manufacturing process of an immunoglobulin.

BRIEF DESCRIPTION OF THE DRAWINGS

FIG. 1: Process Schemes of Conventional Purification Methods for Immunoglobulins FIG. 1A shows a universal process scheme for purification of immunoglobulins from large volumes of cell cultures. The process which started from the clarified bulk material, which is obtained after centrifugation and/or filtration of the harvested culture fluid, consists of a Protein A capture step and two subsequent polishing steps. This scheme includes two typical virus safety steps. A virus inactivation step is performed by keeping the Protein A eluate at low pH and a nanofiltration step for virus removal is performed after the last polishing step. The final step is usually a tangential flow ultrafiltration and/or diafiltration (UF/DF-TFF) to set the desired concentrations of the immunoglobulin and those of the formulation ingredients.

FIG. 1B shows a classical process scheme for purification of immunoglobulins from large volumes of cell cultures consisting of three chromatographies (e.g. according Fahrner R. L. 2001 or Kelly B. 2009). It is the same process as in FIG. 1A except that the polishing steps are disclosed to be a cation exchange chromatography (polishing step 1) followed by an anion exchange chromatography (polishing step 2). It has to be emphasized that the cation exchange chromatography is performed in a binding mode, whereas the anion exchange chromatography is performed in a flow-through mode. It should be mentioned that a frequently applied equivalent variant of this classical scheme is simply to change the order of polishing step 1 and 2.

FIG. 2: Exemplary Process Schemes of the Invention Using Pre-Cleaning Steps

FIG. 2A: Shows a large scale process scheme with pre-cleaning steps before a Protein A capture step. The harvested cell culture fluid is clarified by preparative centrifugation using a separator followed by a depth filtration and a microfiltration. The pre-cleaning chromatography step is performed by using an anion exchange column in the flow-through mode. In a preferred configuration, the pre-cleaning column is directly connected to the capture chromatography column, which is Protein A. The two polishing steps are a cation exchange chromatography utilized in the bind and elute mode (polishing step 1) followed by a Mixed Mode chromatography (polishing step 2). The Mixed Mode resin has positively charged ligands and can be performed either in the binding mode or in the flow-through mode. This second polishing step is optional. The viral safety steps and the final UF/DF-TFF are described under FIG. 1A.

FIG. 2B shows an alternative large scale process scheme which is similar to the process of FIG. 2A except that between the pre-cleaning anion exchange chromatography and the Protein A affinity chromatography a further Mixed Mode chromatography is inserted. This Mixed Mode chromatography is performed either with a resin containing negatively charged ligands (e.g. Capto MMC) or with a resin containing positively charged or uncharged ligands (e.g. MEP HyperCel) and is performed in the binding mode. Therefore, the Mixed Mode chromatography functions as the capture step in this process, whereas the Protein A affinity chromatography is better defined as an intermediate step within this scheme. The second Mixed Mode chromatography step as the last chromatography is optional. All the other steps are as described under FIG. 2A.

FIG. 2C shows a further alternative large scale process scheme which is similar to the process of FIG. 2A except that the Protein A capture chromatography is replaced by a Mixed Mode capture chromatography. This Mixed Mode chromatography is performed either with a resin containing negatively charged ligands (e.g. Capto MMC) or with a resin containing positively charged or uncharged ligands (e.g. MEP HyperCel) and is performed in the binding mode. In contrast to the process shown in FIG. 2B this process is devoid of a Protein A affinity chromatography. All the other steps are as described under FIG. 2A.

DETAILED DESCRIPTION OF THE INVENTION

As used herein, a "sample" or "sample comprising the immunoglobulin and at least one impurity" comprises an immunoglobulin of interest and at least one impurity. The sample can be obtained directly from a host cell or organism producing the immunoglobulin. The sample may be a harvested cell culture fluid, cell culture supernatant or pretreated cell culture supernatant. The sample may have been partially clarified or purified by centrifugation and/or filtration, for example microfiltration, diafiltration, ultrafiltration and depth filtration.

As used herein, the term "pretreated sample" is for example a cell culture supernatant that has been prepared for a chromatography step used in a method of the invention, for example by subjecting the sample to one or more adjustments consisting of buffer exchange, dilution, addition of salts, detergents, chaotropic substances, or organic compounds, pH titration or filtration in order to adjust the pH and/or conductivity range and/or buffering capacity to achieve a desired chromatography performance and to stabilize the immunoglobulin. As immunoglobulins expressed from mammalian cells are usually secreted into the cell culture fluid during the cultivation process, the product harvest at the end of the cultivation process occurs by separating cell culture fluid from the cells. The cell separation method should be gentle to minimize cell disruption to avoid the increase of cell debris and release of proteases and other molecules that could affect the quality of the immunoglobulin product. Usually, the harvest from mammalian cell cultures undergoes centrifugation followed by filtration. Expanded bed adsorption chromatography is an alternative method to avoid centrifugation/filtration methods. Other treatments of the sample prior to the purification via chromatographic steps may be concentrating and/or diafiltrating of the cell culture supernatant into specific immunoglobulin concentration, range of pH, conductivity, and buffer species concentration.

The terms "impurity" and "contaminant" are used interchangeably herein and refer to any material that is different to the immunoglobulin of interest. Examples may be cell culture fluid components, host cell proteins, endotoxins, viruses, lipids, DNA, RNA, leachates from process materials, and aggregates or fragments thereof. Also considered as impurities are aggregates, charge variants, misfolded molecules or fragments of the immunoglobulin of interest to be purified.

As used herein the term "chromatography media" or "chromatography medium" has to be understood as a chromatography material or media in form of beads, plates, crystals, monoliths, membranes, fibers, meshwork of fibers or any other solid phase. The "media" bears functional groups referred to as "ligands" bound to a backbone referred to as "matrix". An exception are gel chromatography resins for size exclusion chromatography which are typically without any attached ligand. Therefore the term "media" does not limit the methods of the invention to only column chromatography employing chromatography resins but also includes other types of chromatography, for example membrane chromatography employing membrane adsorbers. In particular, in anion exchange chromatography an anion chromatography exchange resin or an anion exchange chromatography membrane adsorber are both comprised by the invention.

"Resin" means any chromatographic material or media in form of beads comprising a matrix with a bound functional group (ligand) which may interact with the protein or at least one contaminant. An exception are gel chromatography resins for size exclusion chromatography which are typically without any attached ligand. Resins may be supplied as beads of different sizes and packed in columns. Alternatively, pre-packed columns may be purchased.

The term "binding mode" or "bind and elute mode" refers to chromatography conditions in which a sample containing the immunoglobulin to be purified is applied to a chromatography medium, wherein the immunoglobulin binds to the chromatography medium. Thus, the immunoglobulin is retained on the chromatography medium, whereas the impurities of the sample may be present in the non-binding fraction, also called the flow-through fraction. When a chromatography step is carried out in the binding mode, one or more washing steps may be performed after the binding of the immunoglobulin to the chromatography medium and prior to eluting the immunoglobulin from the medium. To obtain the immunoglobulin, the immunoglobulin is then eluted and obtained in the eluate, which may then further be purified in a further chromatographic step, if desired. Elution of the immunoglobulin may be performed using selective conditions permitting contaminants to remain bound to the medium while the immunoglobulin is eluted.

Performing a chromatography step in the "binding mode" does not necessarily mean that 100% of the immunoglobulin of interest is bound. In the context of the present invention, "bound to the chromatography resin" or "bound to the chromatography medium" means that at least 50% of the immunoglobulin is bound, preferably at least 75% of the immunoglobulin is bound, more preferably at least 85% of the immunoglobulin is bound, and most preferably more than 95% of the immunoglobulin is bound to the resin or medium.

The terms "flow-through mode", "obtaining the immunoglobulin, which is not bound to the chromatography resin, in the flow-through", and "obtaining the immunoglobulin, which is not bound to the chromatography medium, in the flow-through" refer to chromatography conditions in which a sample containing the immunoglobulin of interest is applied to the chromatography resin or medium, wherein the immunoglobulin does not bind to the chromatography resin but is mainly present in the fraction that is not bound to the resin or medium and thus contained in the flow-through.

Performing a chromatography step in the "flow-through mode" does not necessarily mean that 100% of the immunoglobulin of interest is not bound and thus contained in the flow-through. In the context of the present invention, "not bound to the chromatography resin" or "not bound to the chromatography medium" means that at least 50% of the immunoglobulin is not bound, preferably at least 75% of the immunoglobulin is not bound, more preferably at least 85% of the immunoglobulin is not bound, and most preferably more than 95% of the immunoglobulin is not bound to the resin or medium. Impurities may bind to the resin or medium in this mode.

In the context of the present invention, it is understood that the pre-cleaning chromatography step of the invention is performed in the flow-through mode, whereas the capture step is considered to be the first chromatography step which is performed in the binding mode.

In the experiments which lead to the present invention it was observed that the cell-free harvest material (clarified supernatant) still contains several substances that, along with the immunoglobulin to be purified, bind strongly to the capture resin. This affects the re-use of the resin. According to the finding of this invention, the insertion of a suitable pre-cleaning column represents a good solution for additional rapid purification of the clarified culture fluid. By binding further impurities, the pre-cleaning column improves the purity of the sample, reduces critical contaminations, and protects the costly affinity column. The pre-cleaning column should be reusable and its regeneration should be possible by simple means. Most suited are strong anion exchange chromatography media with robust matrices, bearing ligands selected from the group of quaternary aminoethyl, quaternary ammonium or trimethylammonium moieties, for example as provided by Nuvia Q. Using the pre-cleaning anion exchange column in the flow through mode has several advantages: The column can be kept relatively small and it can be directly connected to the capture column. This configuration avoids temporary collection and storage of the anion exchange eluate, reduces the number of steps and improves the process economy. The anion exchange column could be followed either by a Protein A, or a Mixed Mode resin (e.g. Bakerbond ABx, Capto MMC, CaptoAdhere or MEP HyperCel) or any other high-priced resin which is difficult to regenerate.

The term "in the following order" is to be understood to mean that the mentioned process steps are carried out in the listed order. Further process steps may be incorporated before, after and between the listed process steps.

The present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

The present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) either to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

The present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

The present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) either to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

The term "further processing step" refers to any step that is commonly applied within protein purification protocols such as filtration, dialysis, virus inactivation, dilution, concentration, adjustments in pH, adjustments of conductivity, or an intermediate chromatography step. A further processing step can be applied between all chromatography steps of the invention. An intermediate chromatography step can be applied between any of the chromatography steps except between exposing the sample to the anion exchange chromatography of step (a) and exposing the flow-through obtained in step (a) to the chromatography of step (b). In particular, the term "further processing step" refers to an intermediate chromatography step applied between the capture chromatography and the cation exchange chromatography. The intermediate chromatography step may be carried out with any chromatography media. The intermediate chromatography step may employ any chromatography type, including column chromatography and membrane chromatography.

In one embodiment, between exposing the sample to the anion exchange chromatography of step (a) and exposing the flow-through obtained in step (a) to the chromatography of step (b) no further processing step is applied.

In another embodiment, between exposing the sample to the anion exchange chromatography of step (a) and exposing the flow-through obtained in step (a) to the chromatography of step (b) no filtration, e.g. sterile filtration is applied.

Pre-Cleaning Step: Anion Exchange Chromatography

The method of the invention involves as a pre-cleaning step an anion exchange chromatography step in the flow-through mode before the capture step. The anion exchange chromatography medium may be a strong or a weak anion exchange chromatography medium, including anion exchange membranes.

It has been found that this pre-cleaning anion exchange chromatography step is capable of efficiently retaining impurities which may otherwise cause precipitation at acidic pH and of binding host nucleic acid molecules such as DNA and RNA. It has further been found that substances from the crude sample promoting fouling in a chromatographic capture column are pre-captured by the pre-cleaning anion exchange column and withheld from entering the subsequent capture column. Additionally, the pre-cleaning step has a significant effect on Protein A leaching, which could be greatly reduced by using the pre-cleaning chromatography. Finally, it was observed that in cases where precipitations and/or turbidities were observed during the hold step of the Protein A eluate for virus inactivation, this effect was avoided completely when using a pre-cleaning anion exchange chromatography. As the chromatography medium of the pre-cleaning step is exposed to the highest load of impurities in the chromatography process, a fast, cheap and efficient regeneration and cleaning procedure is needed for the chromatography medium of the pre-cleaning step. It has been found that the regeneration of the anion exchange chromatography medium (e.g. resin or membrane) can be efficiently carried out with a fast, cheap and efficient protocol comprising only few steps. For the regeneration of the anion exchange chromatography medium harsh conditions can be employed, that allow cleaning of the chromatography medium in a short time without impairing its function. Ion exchange chromatography relies on charge-charge interactions between the molecules to be bound and the charges immobilized on the matrix. In anion exchange chromatography the molecules to be bound are negatively charged and the immobilized functional groups (ligands) are positively charged. Commonly used anion exchange chromatography media are Q media, (quaternary amine ligands), TMAE resins (trimethylaminoethyl ligands), and DEAE resins (diethylaminoethyl ligands). However, in general the anion exchange chromatography step can be performed with all common commercially available anion exchange media. Anion exchange media may be used in the form of pre-packed columns or as membranes. Alternatively, the resins may be purchased as bulk material and the columns packed by the user. There are no specific limitations as to the capacity and the dimensions of the columns other than the usual ones. The person skilled in the art knows the amount of anion exchange chromatography medium and the size of the column to be used. This depends on the overall scale of the process.

Typical strong anion exchange chromatography media that can be used for the purpose of the invention comprise functional groups such as: quaternary aminoethyl (QAE) moieties, resins include e.g. Toyopearl QAE (available from Tosoh Bioscience, Germany), Selectacel QAE (a quaternary aminoethyl derivative of cellulose, available from Polysciences Inc., Pennsylvania USA), QAE Sephadex (available from GE Healthcare, Germany), and others; quaternary ammonium (Q) moieties, resins include e.g. Q Sepharose XL, Q Sepharose FF, Q Sepharose HP, Q Sepharose CL-4B, Q Sepharose Big Beads, Source Q, Resource Q, Capto Q, Capto Q ImPres (all available from GE Healthcare, Germany), Poros HQ (Applied Biosystems, Germany), Q HyperCel, Biosepra Q Ceramic HyperD (available from Pall, New York, USA) Macro Prep High Q (Bio-Rad, California, USA), Toyopearl Super Q (available from Tosoh Bioscience, Germany), UNOsphere Q (available from Bio-Rad, California, USA), trimethylammoniumethyl (TMAE) include e.g. Fractogel EMD TMAE (Merck KgaA, Germany), and trimethylammonium resins include e.g. Nuvia Q (available from Bio-Rad, California, USA).

In particular, strong anion exchange chromatography media have been found to be effective in retaining impurities that would otherwise cause precipitation at acidic pH and of binding host nucleic acid molecules such as DNA and RNA.

Preferably, strong anion exchange chromatography media comprising a ligand selected from the group consisting of quaternary aminoethyl (QAE) moieties, quaternary ammonium moieties and trimethylammonium moieties except trimethylammonium ethyl bound to a methacrylate polymeric matrix are used.

More preferably, the anion exchange chromatography may be a strong anion exchange chromatography which is performed using a strong anion exchange chromatography resin having —$N(CH_3)_3^+$ (trimethylammonium; Nuvia Q available from Bio-Rad, California, USA) functional groups (ligands), or a medium having similar characteristics.

Thus, a preferred embodiment of the present invention provides a method for purifying an immunoglobulin from a sample comprising the immunoglobulin and at least one impurity, the method comprising the following steps in the following order:

(a) exposing the sample to strong anion exchange chromatography and obtaining the immunoglobulin, which is not bound to the strong anion exchange chromatography resin, in the flow-through;

(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;

(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

The characteristics of the strong anion exchanger Nuvia Q are as follows:

| | |
|---|---|
| Functional group: | —$N(CH_3)_3^+$ |
| Total ionic capacity | 100-170 µeq/ml |
| Dynamic binding capacity | ≥170 mg/ml |
| Shipping counter ion | Cl⁻ |
| Median particle size | 85 ± 15 µm |
| Recommended linear flow rate range | 50-600 cm/hr |
| Chemical stability | |
| 1.0M NaOH (20° C.) | up to 1 week |
| 1.0M HCl (20° C.) | up to 5 weeks |
| Gel bed compression ratio | 1.10-1.15 (settled bed volume/packed bed volume) |
| pH stability | |
| short term | 2-14 |
| long term | 4-12 |
| shipping solution 20% | ethanol + NaCl |
| Regeneration | 1-2M NaCl |

| | |
|---|---|
| Sanitation | 0.5-1.0 NaOH |
| Storage conditions | 20% ethanol or 0.01 NaOH |

In a preferred embodiment, the diameter of the pre-cleaning anion exchange column is greater than the diameter of the capture column. In another preferred embodiment, the bed height of the pre-cleaning anion exchange column is shorter than the bed height of the capture column. In the most preferred embodiment, the diameter of the pre-cleaning column is greater than the diameter of the capture column and the bed height of the pre-cleaning anion exchange column is shorter than the bed height of the capture column. A minimum of about 10 cm bed height for the pre-cleaning anion exchange column is required for optimal capturing of the impurities.

Some types of impurities may bind to the medium not only via ionic interaction, but also via hydrophobic interaction. Complex formation may also occur. Since the pre-cleaning chromatography step functions as a filter for undesired contaminants, which are tightly adsorbed to the medium, it is necessary to develop an effective regeneration and cleaning procedure. In order to remove most of the impurities from the strong anion exchange chromatography resin (e.g. having a —$N(CH_3)^{3+}$ ligand such as Nuvia Q), after its use the following regeneration procedure (cleaning in place) may be used in the following order: (a) Solution A: 40 mM Na phosphate, 2M Urea, 1.5M NaCl, 10 mM EDTA, pH 7-8. (b) Solution B: 2M NaCl, 100 mM citric acid. (c) Solution C: Water (d) Solution D: 1M NaOH. (e) Solution E: 10 mM NaOH. Solutions A-E are passed consecutively through the column. Solution E may be used for storage. It is recommended to carry out the regeneration in reverse flow.

Preferably, the columns of the pre-cleaning and the capture step may be connected in series. This means that the flow-through of the pre-cleaning step is not temporarily stored in a collecting vessel but is immediately passed to the capture chromatography column. In a preferred method, the two columns are disconnected after the run and regenerated separately (cleaning in place). Most preferred regeneration steps are performed in reverse flow.

Capture Step

The term "capture step" is understood as the first chromatography step conducted in the binding mode. The capture step for purification of an immunoglobulin out of culture fluids is usually carried out as an affinity chromatography step. Protein A or derivatives thereof are mostly used as affinity capture. However, also other chromatographic principles may be used as captures step. According the invention Mixed Mode chromatography can be successfully used to capture immunoglobulins.

In a preferred embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In another preferred embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In another preferred embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In another preferred embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;

(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In another preferred embodiment the invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), and obtaining the immunoglobulin in the eluate by eluting the protein from the cation exchange chromatography resin.

In a further preferred embodiment the invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through, wherein the ligand of the strong anion exchange chromatography resin is —N(CH$_3$)$_3^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

Protein a Affinity Chromatography

By using a Protein A affinity chromatography step as the capture step after the anion exchange pre-cleaning chromatography step the method of the invention provides a cost-effective immunoglobulin purification method while taking advantage of the significant binding specificity of Protein A affinity chromatography in the purification of immunoglobulins.

As used herein, the term "immunoglobulin binding protein/peptide affinity chromatography" refers to affinity chromatography which employs as ligands recombinant proteins of microbial origin (e.g. *Staphylococcus aureus*, *Streptococcus*, *Peptostreptococcus magnus*) or variants derived thereof, or synthetic peptides that may be of microbial origin with the ability to bind to immunoglobulins. Exemplary immunoglobulin binding proteins may be Protein A, Protein G, Protein L, or Protein A/G. Preferably, the immunoglobulin binding protein or peptide is Protein A. The ligands can comprise one of more of the E, D, A, B and C domains of Protein A. More preferably the ligands comprise domain B of protein A or the engineered protein Z. An exemplary resin employing as ligand a 14 kD peptide recombinantly produced with *Saccharomyces cerevisiae* is IgSelect (GE Healthcare). This ligand for which no further information is available was specifically designed for high affinity to all types of human Fc.

In order to make the Protein A affinity chromatography material more resistant to harsh cleaning conditions and to provide protection against inter-run cross-contamination effects, it is common today to use improved Protein A affinity resins, bearing ligands specially engineered to ensure alkali tolerance, high binding capacity, and low ligand leakage. One major drawback of these improved resins is, however, that they are significantly costlier than conventional Protein A resins. It is an important advantage of the method of the present invention that both conventional Protein A resins as well as the more recent new generation Protein A resin products can be used. Since the Protein A resins are exposed to a lower impurity burden, conventional and cheaper Protein A resins become acceptable despite their limitation to rather mild regeneration conditions. However, as a result of the pre-cleaning step of the invention and independently from the selected Protein A resin, both conventional and new generation resins can be used over a longer lifetime. Further, due to the fact that the cleaning of the Protein A column becomes easier, the process also becomes more economical.

Examples of common Protein A resins that can be used for the purpose of the invention may include, but are not limited to, Unosphere SUPrA (Bio-Rad), Protein A Ceramic HyperD F (Pall Corporation), Poros MabCapture A (Applied Biosystems), ProSep HC, ProSep Ultra, and ProSep Ultra Plus (EMD Millipore), Protein A Sepharose FF, rProtein A Sepharose FF, rmp Protein A Sepharose FF, MAbSelect, MAbSelect SuRe, MAbSelect SuRe LX, and MabSelect Xtra (GE Healthcare), and Toyopearl rProtein A (Tosoh Bioscience).

When used herein, the term "Protein A" encompasses Protein A recovered from a native source thereof, Protein A produced synthetically or biosynthetically (e. g. by peptide synthesis or by recombinant techniques), and variants thereof which retain the ability to bind proteins which have a CH2/CH3 region. Preferably, resins with high binding capacity and/or alkaline stability may be used. For example, Protein A, Protein A derivative, alkali-stabilized Protein A-derived affinity medium (*E. coli*) may be used. Preferably, alkali-stabilized Protein A-derived (*E. coli*) ligands may be used. The alkali-stabilized, Protein A-derived ligand may be coupled to a highly cross-linked agarose matrix, preferably immobilized with a chemically stable thio-ether linkage. One example is MabSelect SuRe from GE Healthcare Life Sciences which can be rapidly and efficiently cleaned after the run with up to 0.5 M NaOH. The alkali-stabilized ligand of MabSelect SuRe is derived from the B-domain of Protein A and essentially lacks the VH3 binding domain giving a higher elution pH. A preferred product is MabSelect SuRe LX, which has a higher binding capacity than MabSelect SuRe.

The characteristics of the Protein A resin MabSelect SuRe LX are as follows:

| | |
|---|---|
| Matrix | Rigid, highly cross-linked agarose |
| Ligand | Alkali-stabilized, protein A-derived (*E. coli*) |
| Ligand coupling | Single-point attachment |
| Ligand coupling | Epoxy |

| | |
|---|---|
| Average particle size (d$_{50v}$)* | 85 µm |
| Dynamic binding capacity | Approx 60 mg human IgG/ml medium at 6 min residence time |
| Maximum mobile phase velocity | 500 cm/h |
| pH working range | 3-12 |
| Chemical stability | Stable in all aqueous buffers commonly used in protein A chromatography |
| Cleaning-in-place stability | 0.1-0.5M NaOH |
| Delivery conditions | 20% ethanol |

One or several wash steps between the Protein A affinity chromatography and the elution of the immunoglobulin from the Protein A column may be included employing special wash buffer(s). The wash buffer is the buffer used to remove impurities from the Protein A resin without removing significant amounts of the immunoglobulin of interest bound to the Protein A. The wash buffer may comprise salt and detergent (e.g. polysorbate); salt and solvent (e.g. hexylene glycol); high concentration salt (e.g. high molarity Tris buffer); or salt and polymer (e.g. polyethylene glycol). Furthermore, the wash buffer may include chaotropic reagents (e.g. urea or arginine) and/or protease inhibitors (e.g. EDTA).

For the elution of the immunoglobulin of interest from the Protein A column an elution buffer is applied. Preferably, the elution buffer has a low pH and thereby disrupts interactions between Protein A and the immunoglobulin of interest by changing the protein conformation. Preferably, the low pH elution buffer has a pH in the range from about 2 to about 5, most preferably in the range from about 3 to about 4. Examples of buffers that will control the pH within this range include phosphate, acetate, citrate, glycine, and ammonium buffers, as well as combinations of these. Such preferred buffers are citrate and acetate buffers, most preferably sodium citrate or sodium acetate buffers. Other elution buffers are contemplated, including high pH buffers (e.g. those having a pH of 9 or more) or buffers comprising a compound or composition such as MgCl$_2$ (2 mM) for eluting the immunoglobulin of interest.

The Protein A affinity chromatography resin may be regenerated with 0.1 to 0.5 NaOH, preferably within the column (cleaning in place).

In a specific embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized Protein A derivative (e.g. MabSelect SuRe);
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In a further embodiment the invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through; wherein the ligand of the strong anion exchange chromatography is —N(CH$_3$)$_3$$^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is an alkali-stabilized Protein A derivative (e.g. MabSelect SuRe);
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

Mixed Mode Chromatography as Capture Step

In a further embodiment the present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In a further embodiment the present invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

Mixed Mode chromatography (MMC) utilizes more than one form of interaction between the ligand and the molecules of the sample. The resins referred to as Mixed Mode resins are chromatographic materials possessing functional groups consisting of either charged hydrophobic ion exchange ligands or crystalline minerals such as hydroxyapatite. Instead of "Mixed Mode chromatography" the term "multi modal chromatography" or "hydrophobic charge induction chromatography" has sometimes been used. Mixed Mode chromatography is usually an interaction of at least two principles, hydrophobic interaction and ion exchange or metal affinity interaction and ion exchange. Mixed Mode chromatography provides less predictable selectivities that cannot be reproduced by a single mode chromatography method such as ion exchange or hydrophobic interaction chromatography, respectively. Positively charged hydrophobic ligands belong to the group of anion exchanger Mixed Mode (for example Capto MMC), and the negatively charged ligands belong to the cation exchanger Mixed Mode (for example CaptoAdhere). Some Mixed Mode resins have zwitterionic character (for example Bakerbond ABx). Other Mixed Mode resins possess hydrophobic ligands which are ionisable and convert from uncharged to positively charged by lowering the pH (for example MEP HyperCel). Finally, hydroxyapatite resins have more complex Mixed Mode functions by possessing positively charged calcium ions and negatively charged phosphate groups.

Preferably, Mixed Mode resins exhibiting ionic and hydrophobic functionalities are employed e.g. Bakerbond ABx (J.T. Baker), Capto MMC, CaptoAdhere (GE Healthcare), PPA HyperCel, or MEP Hypercel (Pall Corporation). More preferably the Mixed Mode chromatography resin MEP HyperCel is employed.

The characteristics of the Mixed Mode chromatography resin MEP HyperCel are as follows:

| | |
|---|---|
| Particle Size (average) | 80-100 μm |
| Dynamic Binding Capacity for Human IgG (10% breakthrough) | ≥20 mg/ml |
| Ligand | 4-Mercapto-Ethyl-Pyridine |
| Ligand Density | 80-125 μmol/mL |
| Working pH (long-term) | 2-12 |
| Cleaning pH (less than 6 hours) | 2-14 |
| Pressure Resistance | <3 barg (44 psig) |
| Typical Working Pressure | <1 barg (14 psig) |

The Mixed Mode chromatography resin comprising 4-Mercapto-Ethyl-Pyridine as ligand (MEP HyperCel) may be equilibrated with buffer having a pH of about 6.5 to 9.9, for example PBS, pH 7.4 or 50 mM Tris-HCl, pH 8.

For the elution of the immunoglobulin of interest from the Mixed Mode chromatography resin comprising 4-Mercapto-Ethyl-Pyridine as ligand (MEP HyperCel), an elution buffer is applied. Preferably, the elution buffer has a pH that disrupts the interaction of the immunoglobulin of interest and the MEP HyperCel column. Preferably, the elution buffer has a pH in the range from about pH 3 to about pH 7, preferably from about pH 3.5 to about pH 6, more preferably from about pH 4 to about pH 5.5. Arginine (0.1 to 1.0M, 0.2 to 0.8M, 0.4 to 0.6M) may be added to the elution buffer (such as MEP HyperCel elution buffers) thus reducing immunoglobulin aggregation and preventing loss of solubility at acidic pH.

An advantage of Mixed Mode Chromatography is that the immunoglobulin binding to the resin does not require addition of large amounts of salt (such as ammonium sulphate) as is, for example, necessary when using conventional hydrophobic interaction chromatography.

The mild elution condition of Mixed Mode chromatography (such as Mixed Mode chromatography employing a resin comprising 4-Mercapto-Ethyl-Pyridine as ligand) may reduce aggregation and may preserve the biological activity of the immunoglobulin.

The Mixed Mode chromatography resin may be regenerated with 10 to 200 mM citric acid, 10 mM HCl, 0.5 to 1.0M NaOH, 6M guanidine hydrochloride, 2 to 8M urea or 40% propanol. Preferably, by applying the pre-cleaning step, the Mixed Mode chromatography resin may be simply regenerated with 100 mM citric acid followed by 0.5 to 1.0M NaOH.

In a further embodiment, the present invention provides a method for purifying an immunoglobulin from a sample comprising the immunoglobulin and at least one impurity, the method comprising the following steps in the following order:

(a) exposing the sample to anion exchange chromatography and obtaining the immunoglobulin, which is not bound to the anion exchange chromatography resin, in the flow-through;

(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand is 4-Mercapto-Ethyl-Pyridine;

(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In a further embodiment the present invention provides a method for purifying an immunoglobulin from a sample comprising the immunoglobulin and at least one impurity, the method comprising the following steps in the following order:

(a) exposing the sample to strong anion exchange chromatography and obtaining the immunoglobulin, which is not bound to the strong anion exchange chromatography resin, in the flow-through;

(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand is 4-Mercapto-Ethyl-Pyridine;

(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In a further embodiment the present invention provides a method for purifying an immunoglobulin from a sample comprising the immunoglobulin and at least one impurity, the method comprising the following steps in the following order:

(a) exposing the sample to strong anion exchange chromatography and obtaining the immunoglobulin, which is not bound to the strong anion exchange chromatography resin, in the flow-through; wherein the ligand is —N(CH$_3$)$_3$$^+$;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand is 4-Mercapto-Ethyl-Pyridine; (c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the cation exchange chromatography resin, and obtaining the immunoglobulin in the eluate by eluting the protein from the cation exchange chromatography resin.

Preferably, for the Mixed Mode chromatography of step (b) step a Mixed Mode chromatography resin comprising negatively charged ligands may be used. More preferably, the resin comprising negatively charged ligands is a multimodal weak cation exchanger (Capto MMC) with the following formula

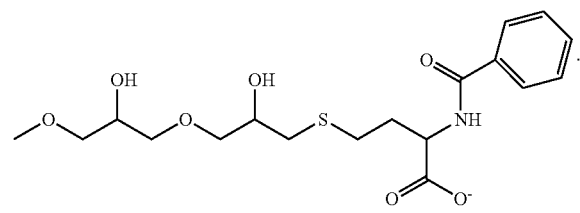 [SMILES: COCC(O)COCC(O)CSCCC(NC(=O)c1ccccc1)C(=O)[O-]]

The characteristics of the multimodal weak cation exchanger Capto MMC are as follows:

| | |
|---|---|
| Ionic Capacity | 0.07-0.09 mmol H+/ml medium |
| Chemical Stability | All commonly used aqueous buffers, 1M acetic acid, 1M sodium hydroxide, 8M urea, 6M guanidine hydrochloride, and 70% ethanol1) |
| Storage Conditions | 4 to 30° C., 20% Ethanol |
| pH Stability Working Range | 2-12 |
| Matrix | Highly cross-linked agarose |
| pH Stability Cleaning-in-Place (CIP) | 2-14 |
| Ion Exchanger Type | Multimodal weak cation exchanger |
| Binding Capacity/ml Chromatography Medium | >45 mg BSA/ml medium at 30 mS/cm2) |

For the elution of the immunoglobulin of interest from the multimodal weak cation exchange chromatography resin pH and/or salt concentration of the buffer may be increased. Preferably, both, pH and salt concentration may be increased. The salt concentration of the elution buffer may range from 0.25M to 1.75M, preferably from 0.5M to 1M. Exemplary salts/buffers used for the elution may be sodium phosphate, Tris-HCl, NaCl and/or NH$_4$Cl. The ionic strength may range from 0.02-0.3M. The pH of the buffer may range between pH 6 and pH 9, preferably between pH 7 and 8, more preferably an additional wash step with pH between 5.5 and 7.5 is applied prior to elution.

In an alternative embodiment, a further polishing step may be employed. The further polishing step may be of any chromatography method suitable for a polishing step such as anion exchange chromatography, cation exchange chromatography, hydrophobic interaction chromatography or mixed mode chromatography.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligands of the Mixed Mode chromatography resin are negatively charged;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the cation exchange chromatography resin, and obtaining the immunoglobulin in the eluate by eluting the protein from the cation exchange chromatography resin.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;

(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the to the cation exchange chromatography resin, and obtaining the immunoglobulin in the eluate by eluting the protein from the cation exchange chromatography resin; wherein the ligand of the Mixed Mode chromatography resin of step (b) has the following formula

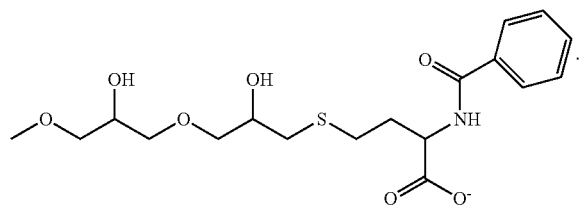 [SMILES: COCC(O)COCC(O)CSCCC(NC(=O)c1ccccc1)C(=O)[O-]]

Cation Exchange Chromatography as Polishing Step

Cation exchange chromatography relies on charge-charge interactions between the proteins in the sample and the charges immobilized on the resin. In cation exchange chromatography, the molecules to be bound are positively charged and the immobilized functional groups (ligands) are negatively charged. Commonly used cation exchange resins are S-resins, (sulphonate), SP resins (sulphopropyl), SE resins (sulphoethyl), and CM resins (carboxymethyl).

However, in general the cation exchange chromatography step can be performed with all common commercially available cation exchange resins or membranes. Cation exchange resins may be used in the form of pre-packed columns or membranes on which the functional group, e.g. sulfonic acid, is fixed. Alternatively, the resins may be purchased as bulk material and the columns packed by the user. There are no specific limitations as to the capacity and the dimension of the columns other than the usual ones. The person skilled in the art knows the amount of cation exchange resin and the size of the column to be used. This depends on the overall scale of the process.

Typical commercially available products include, for example, Macro-Prep High S, Macro-Prep CM, Unosphere Rapid S, Unosphere Rapid S40, Nuvia S, and Nuvia HR-S (Bio-Rad, California, USA), Toyopearl CM, Toyopearl SP, and Toyopearl GigaCap S (Tosoh Bioscience, Germany), Millipore ProRes S, Fractogel EMD COO—, Fractogel EMD SO3- (Merck KGaA, Germany), Biosepra CM Ceramic HyperD, Biosepra S Ceramic HyperD, S HyperCel (Pall Corporation, New York, USA), Poros HS, Poros XS (Applied Biosystems, Germany), YMC BioPro 30S, YMC BioPro 70S (YMC Europe) CM-Sepharose FF, SP-Sepharose FF, S-Sepharose FF, SP-Sepharose HP, SP-Sepharose XL, SP-Sepharose Big Beads, CM-Sephadex, Capto S, Capto SP ImpRes, and Source S (all GE Healthcare, Germany). Commonly, cation exchange chromatography is performed using buffers at pH values between 4 and 7.

Preferred cation exchange resins of this invention are strong cation exchangers using sulfonate or sulfopropyl ligands. Most preferred are sulfonate or sulfopropyl ligands linked to rigid matrices such as highly cross-linked agarose, e.g. Nuvia HR-S, or poly(styrenevinylbenzene), e.g. Poros 50 HS.

The characteristics of the cation exchanger Poros 50 HS are as follows:

| Support Matrix | Crosslinked poly(styrenedivinylbenzene) |
| --- | --- |
| Surface Functionality | Sulfopropyl ($-CH_2CH_2CH_2SO_3^-$) |
| Dynamic Binding Capacity @1000 cm/hr | Lysozyme, pH 6.2 55 mg/ml |
| Shrinkage/Swelling | <1% from 0-100% solvent |
| Particle Size | 50 μm |
| Recommended maximum flow rate in 10 cm bed length | 1,000 cm/hr |
| Mechanical resistance | 100 bar (1500 psi, 10 MPa) |
| Media backpressure | <3 bar at 1,000 cm/hr (10 cm bedheight) |

An alternative preferred material to Poros 50 HS is Nuvia HR-S, a strong cation exchanger based on sulfonate groups and a highly cross-linked agarose matrix.

The cation exchange chromatography may be equilibrated with a buffer having a pH of about pH 4 to about pH 8. The buffer concentration may be in the range of 10 mM to 100 mM, preferably in the range of 20 mM to 50 mM.

Examples of buffers used for cation exchange chromatography are citric acid, lactic acid, formic acid, butanedioic acid, acetic acid, malonic acid, glycine, MES, phosphate, HEPES, or mixtures thereof.

The cation exchange chromatography step may separate charge variants of the immunoglobulin and may remove residual host cell proteins, aggregates and leached Protein A.

The immunoglobulin may bind to the resin at a pH value below the isoelectric point (pI) of the immunoglobulin and at low conductivity.

For elution, an increase in the ionic strength of the elution buffer may be used, provided either by a single step or a gradient. Exemplary salts used in elution of cation exchange chromatography are NaCl, KCl, sulfate salts, phosphate salts, formate salts, or acetate salts. Preferably, NaCl or KCl are used. The ionic strength may be increased to up to 1M.

Alternatively, an increase in the pH of the elution buffer may be used, provided either by a single step or a gradient.

A preferred embodiment for the performance of the cation exchange chromatography is a pH working range between 4 and 6, more preferably a pH range between 4.5 and 5.5. Carbonic acids as buffer substances may be used, citric acid being most preferred.

In a further preferred embodiment, the elution of immunoglobulin bound to the cation exchange resin is performed by a change in the pH value, i.e. an increase in pH. This may be achieved by a gradient from low pH to high pH provided by mixing of two different buffer solutions. Preferred are the citrate buffers for the low pH and phosphate buffers for the high pH. In the most preferred embodiment, the pH gradient is formed by mixing a citrate buffer of about pH 5 to 6 with a phosphate buffer of about pH 7 to 9. The buffers may be prepared by using the Na salts of the acids at a concentration of 10 to 50 mM.

Alternatively, an increase in both the pH and ionic strength of the elution buffer may be used for elution, provided either by a single step or a gradient.

The cation exchange chromatography resin may be regenerated with 1M NaCl for 3 to 5 column volumes. Further, a cleaning in place procedure may be applied comprising the following steps: (a) washing with 1 to 5 column volumes of 1M NaOH, 1M NaCl, (b) washing with 1 to 5 column volumes of 1M acetic acid or TFA, (c) re-equilibration.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin, wherein the ligand of the cation exchange chromatography resin is sulfopropyl.

In a further embodiment, the invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin, wherein the ligand of the cation exchange chromatography resin is sulfopropyl.

In a further embodiment, the invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through; wherein the ligand of the strong anion exchange chromatography resin is —N(CH$_3$)$_3^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin, wherein the ligand of the cation exchange chromatography resin is sulfopropyl.

In a further embodiment, the invention provides a method for purifying an immunoglobulin from a sample comprising the immunoglobulin and at least one impurity, the method comprising the following steps in the following order:
(a) exposing the sample to strong anion exchange chromatography and obtaining the immunoglobulin, which is not bound to the strong anion exchange chromatography resin, in the flow-through, wherein the ligand of the strong anion exchange chromatography resin is —N(CH$_3$)$_3^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin, wherein the ligand of the Protein A affinity chromatography resin is an alkali-stabilized protein A derivative (e.g. MabSelect SuRe);
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin, wherein the ligand of the cation exchange chromatography resin is sulfopropyl.

In another embodiment, the pre-cleaning step of the invention is followed by Mixed Mode chromatography carried out in the binding mode, followed by protein/peptide affinity chromatography carried out in the binding mode.

In another embodiment, the pre-cleaning step of the invention is followed by Mixed Mode chromatography carried out in the binding mode, followed by Protein A affinity chromatography carried out in the binding mode.

Details about Protein A affinity chromatography are provided above and also apply to Protein A chromatography which follows Mixed Mode chromatography.

Details about immunoglobulin binding protein/peptide affinity chromatography are provided above and also apply to Protein A affinity chromatography which follows Mixed Mode chromatography.

Mixed Mode Chromatography as Additional Polishing Step

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography and obtaining the immunoglobulin, which is not bound to the Mixed Mode chromatography resin, in the flow-through.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography and obtaining the immunoglobulin, which is not bound to the Mixed Mode chromatography resin, in the flow-through; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through; wherein the ligand of the anion exchange chromatography is —N(CH$_3$)$_3^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized protein A derivative;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through; wherein the ligand of the anion exchange chromatography is —N(CH$_3$)$_3^+$;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized protein A derivative;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through; wherein the ligand of the anion exchange chromatography is $-N(CH_3)_3^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized protein A derivative;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography and obtaining the immunoglobulin, which is not bound to the Mixed Mode chromatography resin, in the flow-through; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through; wherein the ligand of the anion exchange chromatography is $-N(CH_3)_3^+$;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography and obtaining the immunoglobulin, which is not bound to the Mixed Mode chromatography resin, in the flow-through; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized protein A derivative;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography and obtaining the immunoglobulin, which is not bound to the Mixed Mode chromatography medium, in the flow-through; wherein the ligand of the Mixed Mode chromatography resin is a multimodal strong anion exchanger.

In a further embodiment, the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography and obtaining the immunoglobulin, which is not bound to the Mixed Mode chromatography medium, in the flow-through; wherein the ligand of the Mixed Mode chromatography resin is a multimodal strong anion exchanger.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography and obtaining the immunoglobulin, which is not bound to the Mixed Mode chromatography resin, in the flow-through.

In a further embodiment the present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand is 4-mercapto-ethyl-pyridine;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin.

In a further embodiment the present invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand is 4-Mercapto-Ethyl-Pyridine;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate obtained in step (c) to Mixed Mode chromatography and obtaining the immunoglobulin, which is not bound to the Mixed Mode chromatography resin, in the flow-through.

The media referred to as Mixed Mode media or resins are chromatographic media possessing functional groups consisting of either charged hydrophobic ion exchange ligands or crystalline minerals such as hydroxyapatite. Instead of "Mixed Mode chromatography" the term "multi modal chromatography" or "hydrophobic charge induction chromatography" has sometimes been used. Mixed Mode chromatography is an interaction of at least two principles, hydrophobic interaction and ion exchange or metal affinity interaction and ion exchange. Mixed Mode chromatography provides less predictable selectivities that cannot be reproduced by a single mode chromatography method such as ion exchange or hydrophobic interaction chromatography, respectively. Positively charged hydrophobic ligands belong to the group of anion exchanger Mixed Mode (for example Capto MMC), and the negatively charged ligands belong to the cation exchanger Mixed Mode (for example CaptoAdhere). Some Mixed Mode media have zwitterionic character (for example Bakerbond ABx). Other mixed mode media possess hydrophobic ligands which are ionisable and convert from uncharged to positively charged by lowering the pH (for example MEP HyperCel). Finally, hydroxyapatite media have more complex Mixed Mode functions by possessing positively charged calcium ions and negatively charged phosphate groups.

Preferably, the mixed mode chromatography step following the cation exchange chromatography is performed with a medium comprising positively charged ligands. More preferably, the positively charged ligand is N-benzyl-N-methyl ethanol amine with the following formula:

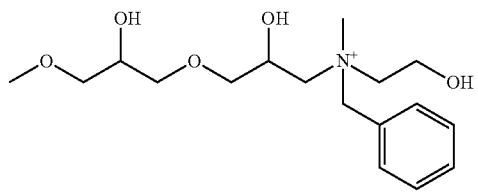 [SMILES: COCC(O)COCC(O)C[N+](C)(CCO)Cc1ccccc1]

(for example CaptoAdhere from GE Healthcare, Germany).

The characteristics of the Mixed Mode chromatography resin CaptoAdhere are as follows:

| | |
|---|---|
| Matrix | highly cross-linked agarose |
| Functional group | multimodal strong anion exchanger |
| Total ionic capacity | 0.09-0.12 mmol Cl−/ml medium |
| Particle size | 75 μm (d50v) |
| Flow velocity | at least 600 cm/h in a 1 m diameter column with 20 cm bed height at 20° C. using process buffers with the same viscosity as water at <3 bar (0.3 MPa). |
| pH stability | |
| short term | 2-14 |
| long term | 3-12 |
| Working temperature | 4 to 30° C. |
| Chemical stability | all commonly used aqueous buffers, 1M acetic acid, 1M sodium hydroxide |
| Avoid | oxidizing agents, anionic detergents |

The following conditions may be applied when loading the mixed mode chromatography resin CaptoAdhere in the bind end elute mode: pH 6 to pH 9, preferably pH 7.0 to 8.5; conductivity 0.5 to 10 mS/cm, preferably 1 to 4 mS/cm. One or more washing steps may be used. The conditions depend on the pI of the immunoglobulin.

The preferred loading conditions for the CaptoAdhere chromatography may be as follows: The resin is equilibrated with 0.5M Na-phosphate, pH 8.2 followed by 20 mM Na-phosphate, pH 8.2. The sample (cation exchange pool) is adjusted to pH 8.0-8.5 and a conductivity of 1-4 mS/cm and loaded onto the column. After washing with the equilibration buffer 20 mM Na-phosphate, pH 8.2 the immunoglobulin of interest may be eluted from the CaptoAdhere resin, for example with 20 mM Na-phosphate, pH 5 to 7, preferentially pH 5.5 to 6.5.

In the flow-through mode the pH and the ionic strength have to be adjusted in such a way that the immunoglobulin does not bind to the Mixed mode ligand while residual contaminants to be cleared (DNA, aggregates, leached Protein A, host cell proteins) remain bound. The conditions depend on the pI of the immunoglobulin. Preferably, phosphate or Tris buffers are used in a pH range of 6.5 to 8.5, more preferably between pH 7 and 8. Conductivity is adjusted with salt, such as NaCl or by buffer concentration. Most preferred is a Na-phosphate buffer in the concentration range of 10 to 50 mM supplemented with NaCl in the concentration range of 50 to 200 mM. It has to be considered that high salt concentrations, although desorbing the ionic interaction, promote the hydrophobic interaction. In a preferred method, the eluate from the cation exchange chromatography is adjusted to pH 7.5 to 8 and the conductivity was raised with NaCl to be 10-12 mS/cm.

The regeneration (cleaning in place) for the Mixed Mode resin may be performed with low pH, high salt, and high pH, e.g. with 10 to 200 mM citric acid, 0.5-2M NaCl, and 10 mM to 1M NaOH.

The preferred regeneration procedure is performed by washing consecutively with solutions A-D: Solution A: 100 mM citric acid, 2M NaCl; Solution B: 2M NaCl; Solution C: 1M NaOH; Solution D: 10 mM NaOH. The storage of the resin may be performed in Solution D.

In a further embodiment, the invention provides a method for purifying an immunoglobulin from a sample comprising the immunoglobulin and at least one impurity, the method comprising the following steps in the following order:

(a) exposing the sample to anion exchange chromatography and obtaining the immunoglobulin, which is not bound to the anion exchange chromatography resin, in the flow-through; wherein the ligand of the anion exchange chromatography is —N(CH$_3$)$_3^+$;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized protein A derivative;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is N-benzyl-N-methyl ethanol amine.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through; wherein the ligand of the anion exchange chromatography is —N(CH$_3$)$_3^+$;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is N-benzyl-N-methyl ethanol amine.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin; wherein the ligand of the Protein A affinity chromatography resin is alkali-stabilized protein A derivative;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is N-benzyl-N-methyl ethanol amine.

In a further embodiment the invention provides a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange medium, in the flow-through;
(b) exposing the flow-through obtained in step (a) to immunoglobulin binding protein/peptide affinity chromatography, wherein the immunoglobulin is bound to the immunoglobulin binding protein/peptide affinity chromatography resin, and obtaining the immunoglobulin in the eluate by eluting the protein from the immunoglobulin binding protein/peptide affinity chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin; wherein the ligand of the cation exchange chromatography is sulfopropyl;
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin; wherein the ligand of the Mixed Mode chromatography resin is N-benzyl-N-methyl ethanol amine.

As polishing step, also other chromatography types can be employed. For example, anion exchange column chromatography and anion exchange membrane chromatography may be employed as polishing step, most preferred being the flow-through mode.

Isoelectric point or pI of a protein refers to the pH at which the protein has a net overall charge equal to zero, i.e. the pH at which the protein has an equal number of positives and negative charges. Determination of the pI may be accomplished according to techniques established in the prior art, such as isoelectric focusing.

In a further embodiment, the purification may include one or more centrifugation steps preceding the first chromatography step.

In another embodiment, the purification may include one or more filtration steps preceding the first chromatography step. In a further preferred embodiment, the purification may include one centrifugation step and one or more filtration steps. In a preferred embodiment, the first chromatography step is preceded by a depth filtration and a microfiltration step. In a more preferred embodiment, the first chromatography step is preceded by a cell separation step, a depth filtration step and a microfiltration step.

In a further embodiment, the invention provides a method for purifying an immunoglobulin from a sample comprising the immunoglobulin and at least one impurity, the method comprising the following steps in the following order:
(i) centrifuging the sample, wherein the immunoglobulin is obtained in the supernatant;
(ii) depth filtrating the supernatant obtained in step (i), wherein the immunoglobulin is obtained in the filtrate;
(iii) micro filtrating the immunoglobulin obtained in step (ii); wherein the immunoglobulin is obtained in the filtrate;
(a) exposing the filtrate of step (iii) to anion exchange chromatography and obtaining the immunoglobulin, which is not bound to the anion exchange chromatography resin, in the flow-through;
(b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin.

In a further embodiment the invention provides a method for purifying an immunoglobulin from a sample comprising the immunoglobulin and at least one impurity, the method comprising the following steps in the following order:
(i) centrifuging the sample, wherein the immunoglobulin is obtained in the supernatant;
(ii) depth filtrating the supernatant obtained in step (i), wherein the immunoglobulin is obtained in the filtrate;
(iii) micro filtrating the immunoglobulin obtained in step (ii); wherein the immunoglobulin is obtained in the filtrate;
(a) exposing the filtrate of step (iii) to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the cation exchange chromatography resin, and obtaining the immunoglobulin in the eluate by eluting the protein from the cation exchange chromatography resin.
(d) exposing the eluate obtained in step (c) to Mixed Mode chromatography, wherein the immunoglobulin is bound to the Mixed Mode chromatography resin, and obtaining the immunoglobulin in the eluate by eluting the protein from the Mixed Mode chromatography resin;

In a further embodiment the invention provides a method for purifying an immunoglobulin from a sample comprising the immunoglobulin and at least one impurity, the method comprising the following steps in the following order:
(i) centrifuging the sample, wherein the immunoglobulin is obtained in the supernatant;
(ii) depth filtrating the supernatant obtained in step (i), wherein the immunoglobulin is obtained in the filtrate;
(iii) micro filtrating the immunoglobulin obtained in step (ii); wherein the immunoglobulin is obtained in the filtrate;
(a) exposing the filtrate of step (iii) to anion exchange chromatography and obtaining the immunoglobulin, which is not bound to the anion exchange chromatography resin, in the flow-through;
(b) exposing the flow-through obtained in step (a) to Mixed Mode chromatography, wherein the immunoglobulin is bound to the Mixed Mode chromatography resin, and obtaining the immunoglobulin in the eluate by eluting the protein from the Mixed Mode chromatography resin;
(b2) exposing the flow-through obtained in step (b) to Protein A affinity chromatography, wherein the immunoglobulin is bound to the Protein A affinity chromatography resin, and obtaining the immunoglobulin in the eluate by eluting the protein from the Protein A affinity chromatography resin;
(c) exposing the eluate obtained in step (b2), or a composition derived therefrom and obtained after one or more further processing steps performed after step (b2), to cation exchange chromatography, wherein the immunoglobulin is bound to the cation exchange chromatography resin, and obtaining the immunoglobulin in the eluate by eluting the protein from the cation exchange chromatography resin.
(d) exposing the eluate obtained in step (c) to Mixed Mode chromatography and obtaining the immunoglobulin, which is not bound to the Mixed Mode chromatography resin, in the flow-through.

Depth Filtration

Further, the method of the invention may comprise one or more depth filtration steps. In contrast to membrane filters which separate by retaining the particles on the surface of a membrane, depth filters consist of a matrix of fibers or beads, wherein separation takes place throughout the matrix rather than on its surface.

Examples of depth filters include, but are not limited to, SXLP700416 and SXLPDE2408SP filter capsules (Pall Corporation), Millistak+ XOHC, FOHC, DOHC, AlHC, and BlHC Pod filters (EMD Millipore), or Zeta 20 Plus 30ZA/60ZA, 60ZN90ZA, delipid, VR07, and VR05 filters (3M).

Preferably, the depth filter is composed of pre-extracted inorganic filter aid, cellulose and a resin system that imparts a strong positive charge to the filter matrix, as for example Zeta Plus from 3M, United Kingdom.

The most preferred depth filters used for this invention are the filter capsules of the PDE2 and P700 series from Pall Corporation.

Ultrafiltration, Virus Filtration, Microfiltration

Further, the method of the invention may comprise one or more microfiltration, ultrafiltration and/or nanofiltration steps. Ultrafiltration is a form of membrane filtration in which hydrostatic pressure forces a liquid against a semipermeable membrane. Suspended solids and solutes of high molecular weight are retained, while water and low molecular weight solutes pass through the membrane. Ultrafiltration is a commonly used method for separation, purifying and concentrating macromolecular solutions, especially protein solutions. Ultrafiltration may be combined with diafiltration. This mode is suitable for buffer exchange, to remove salts and other microspecies from the solution via repeated or continuous dilution and re-concentration. Ultrafiltration may be performed with stacked membranes in a tangential flow or cross flow filtration system (TFF or TF-UF), especially for processing large sample volumes. Alternatively, hollow fiber systems are commonly used for ultrafiltration. Membrane cut-off sizes range from about 1 to 300 kD. For immunoglobulins, typical cut offs for the ultrafiltration membranes are 10-100 kD. In the framework of the present invention, a molecular weight cut off of 30 or 50 kD for the UF membranes is preferred.

Microfiltration is a particle filtration method using membranes with pore sizes from about 0.1 to 10 µm. For sterile filtration, which puts special requirements on the environment, sterilized micro filters are used with pore sizes about 0.2 µm. The use of additional pre-filters with larger pore sizes (0.45 µm, 3 µm) is common. This prevents the decrease in flow by rapid blocking of the small pore sized filters.

Finally, in biopharmaceutical production nanofiltration is predominantly used for viral filtration and is required for the safety of therapeutic proteins produced in mammalian cell cultures. Nanofiltration steps are usually performed at the end of downstreaming close to filling of the bulk of purified immunoglobulin. The pore sizes of the frequently used nanofilters range between 15 and 35 nm (Planova, Asahi Kasei, Japan; or Viresolve, EMD-Millipore, Germany).

In a preferred embodiment of the invention, the process of purification comprises one or more ultrafiltration/diafiltration and/or nanofiltration steps. These filtration steps can be performed using commercially available filtration devices, e.g. available from Pall Corporation, GE Healthcare, EMD-Millipore, or Sartorius.

In another embodiment, the method comprises a further step of incubating the eluate of the Protein A affinity chromatography at low pH of 2.5 to 4.5, preferably pH 3 to 4, for a defined time, preferably 30 to 90 min.

In another embodiment, the method comprises a further step of incubating the eluate of the Mixed Mode chromatography at low pH of 2.5 to 4.5, preferably pH 3 to 4, for a defined time, preferably 30 to 90 min.

In a further embodiment the method comprises a further step of exposing the eluate obtained from the cation exchange chromatography step, or a composition derived therefrom and obtained after one or more further processing steps performed after the cation exchange chromatography step to nanofiltration. Preferably filters with pore sizes of 15 to 35 nm, most preferably 20 nm, may be applied for the nanofiltration.

The anion exchange chromatography step in the flow-through mode may result in a $\log_{10}$ reduction factor of at least 5, of at least 5.5, of at least 6, of at least 6.5 with respect to viruses.

The step of incubation of the eluate (obtained from the Protein A affinity chromatography step or Mixed Mode chromatography step) at low pH may result in a $\log_{10}$ reduction factor of at least 5, preferably of at least 5.5 with respect to enveloped viruses.

The cation exchange chromatography step may result in a $\log_{10}$ reduction factor of at least 5 with respect to enveloped viruses.

The nanofiltration step may result in a $\log_{10}$ reduction factor of at least 4 for enveloped viruses and/or in a $\log_{10}$ reduction factor of at least 5 for non-enveloped viruses.

The cation exchange chromatography step and the step of incubation of the eluate (obtained from the Protein A affinity chromatography step or Mixed Mode chromatography step) at low pH may result in a $\log_{10}$ reduction factor of at least 10 with respect to enveloped viruses.

The anion exchange chromatography step and the step of incubation of the eluate (obtained from the Protein A affinity chromatography step or Mixed Mode chromatography step) at low pH may result in a cumulative $\log_{10}$ reduction factor of at least 10, preferably of at least 11, more preferably of at least 12 with respect to enveloped viruses.

The anion exchange chromatography step, the step of incubation of the eluate (obtained from the Protein A affinity chromatography step or Mixed Mode chromatography step) at low pH and the nanofiltration step may result in a cumulative $\log_{10}$ reduction factor of at least 15, preferably of at least 16 with respect to enveloped viruses.

The anion exchange chromatography step, the step of incubation of the eluate (obtained from the Protein A affinity chromatography step or Mixed Mode chromatography step) at low pH and the cation exchange chromatography step may result in a cumulative $\log_{10}$ reduction factor of at least 15, preferably of at least 16, more preferably of at least 17 with respect to enveloped viruses.

The anion exchange chromatography step, the step of incubation of the eluate (obtained from the Protein A affinity chromatography step or Mixed Mode chromatography step) at low pH, the cation exchange chromatography step and the nanofiltration step may result in a cumulative $\log_{10}$ reduction factor of at least 20, preferably of at least 21 with respect to enveloped viruses.

The anion exchange chromatography step, the cation exchange chromatography step and the nanofiltration step may result in a cumulative $\log_{10}$ reduction factor of at least 12, preferably of at least 13 with respect to non-enveloped viruses.

A specific embodiment relates to a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) incubating the eluate obtained in step (b) at low pH of 2.5 to 4.5 for a defined time;
wherein the method results in a cumulative $\log_{10}$ reduction factor for steps (a) and (c) of at least 10 with respect to enveloped viruses.

A further embodiment refers to a method for purifying an immunoglobulin from a sample comprising the immunoglobulin and at least one impurity, the method comprising the following steps in the following order:

(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) incubating the eluate obtained in step (b) at low pH of 2.5 to 4.5 for a defined time;
(d) exposing the eluate after the incubation of step (c), or a composition derived therefrom and obtained after one or more further processing steps performed after step (c), to nanofiltration;
wherein the method results in a cumulative $\log_{10}$ reduction factor for steps (a) and (d) of at least 10 with respect to non-enveloped viruses and/or wherein the method results in a cumulative $\log_{10}$ reduction factor of steps, (a), (c) and (d) of at least 15 with respect to non-enveloped viruses and/or enveloped viruses.

A further embodiment refers to a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) incubating the eluate obtained in step (b) at low pH of 2.5 to 4.5 for a defined time;
(c2) exposing the eluate obtained in step (c), or a composition derived therefrom and obtained after one or more further processing steps performed after step (c), to cation exchange chromatography, wherein the immunoglobulin is bound to the cation exchange chromatography resin, and obtaining the immunoglobulin in the eluate by eluting the protein from the cation exchange chromatography resin;
wherein the method results in a cumulative $\log_{10}$ reduction factor for steps (a), (c) and (c2) of at least 15 with respect to enveloped viruses.

A further embodiment refers to a method for purifying an immunoglobulin from a sample comprising the immunoglobulin and at least one impurity, the method comprising the following steps in the following order:
(a) exposing the sample to anion exchange chromatography and obtaining the immunoglobulin, which is not bound to the anion exchange chromatography resin, in the flow-through;
(b) exposing the flow-through obtained in step (a) to Protein A affinity chromatography, wherein the immunoglobulin is bound to the Protein A affinity chromatography resin, and obtaining the immunoglobulin in the eluate by eluting the protein from the Protein A affinity chromatography resin;
(c) incubating the eluate obtained in step (b) at low pH of 2.5 to 4.5 for a defined time;
(c2) exposing the eluate obtained in step (c), or a composition derived therefrom and obtained after one or more further processing steps performed after step (c), to cation exchange chromatography, wherein the immunoglobulin is bound to the cation exchange chromatography resin, and obtaining the immunoglobulin in the eluate by eluting the protein from the cation exchange chromatography resin;
(d) exposing the eluate after the incubation of step (c2), or a composition derived therefrom and obtained after one or more further processing steps performed after step (c2), to nanofiltration;
wherein the method results in a cumulative $\log_{10}$ reduction factor for steps (a), (c) and (c2) of at least 15 with respect to enveloped viruses and/or in a cumulative $\log_{10}$ reduction factor for steps (a), (c), (c2) and (d) of at least 20 with respect to enveloped viruses and/or in a cumulative $\log_{10}$ reduction factor for steps (a), (c2) and (d) of at least 12 with respect to non-enveloped viruses.

A further embodiment refers to a method for purifying an immunoglobulin from a sample comprising the immunoglobulin and at least one impurity, the method comprising the following steps in the following order: (a) exposing the sample to anion exchange chromatography and obtaining the immunoglobulin, which is not bound to the anion exchange chromatography resin, in the flow-through; (b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
and exposing the eluate obtained in step (b), or a composition derived therefrom and obtained after one or more further processing steps performed after step (b), to nanofiltration;
wherein the method results in a cumulative $\log_{10}$ reduction factor for steps a) and d) of at least 10 with respect to enveloped viruses and/or non-enveloped viruses.

A further embodiment refers to a method for purifying an immunoglobulin from a sample comprising the immunoglobulin and at least one impurity, the method comprising the following steps in the following order: (a) exposing the sample to anion exchange chromatography and obtaining the immunoglobulin, which is not bound to the anion exchange chromatography resin, in the flow-through; (b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
(c2) exposing the eluate obtained in step (b), or a composition derived therefrom and obtained after one or more further processing steps performed after step (b), to cation exchange chromatography, wherein the immunoglobulin is bound to the cation exchange chromatography resin, and obtaining the immunoglobulin in the eluate by eluting the protein from the cation exchange chromatography resin;
and exposing the eluate obtained in step (c2), or a composition derived therefrom and obtained after one or more further processing steps performed after step (c2), to nanofiltration;
wherein the method results in a cumulative $\log_{10}$ reduction factor for steps a), c2) and d) of at least 15 with respect to enveloped viruses and/or wherein the method results in a cumulative log 10 reduction factor of steps, (a), (c2) and (d) of at least 13 with respect to non-enveloped viruses.

The above described methods also serve for increasing the viral safety in a manufacturing process of an immunoglobulin.

The term incubation "for a defined time" as referred herein refers to incubation for at least 30 min, for at least 40 min for at least 50 min and at least 60 min, preferably to incubation for 30 min to 90 min, more preferably for 45 min to 75 min, most preferably for 60 min.

The pH of the step "incubation at a low pH" refers not only to pH of 2.5 to 4.5, but also refers to a pH of 3 to 4, preferably of 3.25 to 3.75 more preferably to a pH of 3.5.

The term "enveloped virus" refers to any of the viruses with a lipoprotein envelope surrounding the nucleoprotein core of the virus for example to Herpesviruses, Cytoviruses, Poxviruses, Arenaviruses, Arteriviruses, Hepadnaviruses, Flaviviruses, Togaviruses, Coronaviruses, Orthomyxoviruses, Paramyxoviruses, Rhabdoviruses, Bunyaviruses, Filoviruses, Baculoviruses, Iridoviruses, and Retroviruses, including human pathogens and the model virus Murine Leukemia Virus (MuLV) which was used in the experiments.

The term "non-enveloped virus" refers to any of the viruses lacking the viral envelope for example to Adenoviruses, Cauliomoviruses, Myoviruses, Phycodnaviruses, Tectiviruses, Papovaviruses, Circoviruses, Parvoviruses, Birnaviruses, Reoviruses, Astroviruses, Caliciviruses, Picornaviruses, Potyviruses, Tobamaviruses, Carlaviruses, Anelloviruses, and Hepeviruses, including human pathogens and the model virus Minute Virus of Mice (MVM), which was used in the experiments.

The calculated ratio of the viral titer in the starting material and in the relevant product fraction defines the viral reduction, called $\log_{10}$ reduction factor (LRF), $\log_{10}$ reduction value (LRV), or sometimes simply $\log_{10}$ clearance. The mode of the LRF calculation is outlined in the relevant guidelines for viral clearance studies (e.g. (Appendix II of EMA guideline CPMP/BWP/268/95 (1996) "Note for guidance on virus validation studies: the design, contribution and interpretation of studies validating the inactivation and removal of viruses").

$$\text{Log}_{10} \text{ reduction factor} := \frac{\text{Virus concentration in sample load (spiked)}}{\text{Virus concentration in product fraction (after the step)}}$$

The "wash step" is a step performed after the sample is loaded onto the chromatography column, but before the protein is eluted from the column. The wash step additionally removes contaminants less tightly or nonspecifically bound to the matrix, to the immunoglobulin, and/or to the ligand, without significantly eluting the immunoglobulin of interest from the resin. In the wash step, the resin is washed with the desired wash buffer (e. g. the wash buffer is passed through the chromatography column until the UV absorption measured in the outlet of the column returns to baseline).

The term "elution" is understood as a process which desorbs an immunoglobulin of interest from a chromatography resin by altering the solution conditions such that buffer components compete with the molecule of interest for the ligand site on the chromatography resin. Another mode of elution occurs in affinity chromatography, for example using Protein A. In this case, the elution buffer may alter the conformation of the ligand or the immunoglobulin, thereby loosening the binding. An immunoglobulin of interest may be eluted from ion exchange resins by altering the ionic strength of the buffer surrounding the ion exchange material such that the buffer ions in the mobile phase compete with the molecule for the charged ionic sites of the ion exchange resin. Alternatively, a change in the pH influences the amphoteric protein and a pH increase above the pI of the protein henceforth prevent its binding to a cation exchange resin and the protein elutes. The same effect occurs on an anion exchange chromatography resin when the pH is decreased below the pI of the protein.

As understood herein the term "elution" comprises isocratic elution, single step elution, and gradient elution, with or without preceding wash steps. The elution of the immunoglobulin of interest may be conducted by increasing the ionic strength or conductivity in the mobile phase, which is affected by increasing the salt concentration in the buffer solution. Alternatively, an increase or decrease in the pH value may be suitable. Discontinuous step gradients, linear gradients, non-linear gradients or a suitable combination of such gradients may be employed.

Buffers suitable for washing and for the elution can be selected from acetate, citrate, Tris/HCl, Tris/acetate, phosphate, succinate, malonate, MES, HEPES, Bistris, glycine, and other suitable buffers with the addition of salts such as phosphates, sulfates, or chlorides, such as NaCl or KCl. The ionic strength and the salt concentration, by means of which the elution is achieved, are dependent on the pH value of the buffer solution and the pI of the protein. The wash buffer may further comprise detergent (e.g. polysorbate), solvent (e.g. hexylene glycol, ispropanol, or ethanol), or polymer (e.g. polyethylene glycol). Furthermore, the wash buffer may include chaotropic reagents (e.g. urea or arginine) and/or protease inhibitors (e.g. EDTA).

As used herein the term "buffer" refers to a solution that resists changes in the pH by the action of acid-base conjugate components.

The terms "immunoglobulin" and "antibody" are used interchangeably herein. The immunoglobulin may be a monoclonal antibody, polyclonal antibody, multispecific antibody (e.g. bispecific antibody) and fragments thereof exhibiting the desired antigen binding activity. Naturally occurring antibodies are molecules with varying structures. For example, native IgG antibodies are hetero tetrameric glycoproteins of about 150,000 Daltons, composed of two identical light chains and two identical heavy chains that are linked by disulfide bonds. From N- to C-terminus, each heavy chain has a variable domain (VH), also called a variable heavy domain or a heavy chain variable domain followed by three or four constant domains (CH1, CH2, CH3 and optionally CH4). Similarly, from N- to C-terminus, each light chain has a variable domain (VL), also called a variable light domain or a light chain variable domain followed by a constant light chain (CL) domain. The light chain of an antibody may be assigned to one of two types, called kappa (κ) and lambda (λ), based on the amino acid sequence of its constant domain.

"Antibody fragments" comprise a portion of a full length antibody, generally the antigen binding or variable region thereof. Examples of antibody fragments include Fab, Fab', F(ab')2, and Fv fragments; single-chain antibody molecules; diabodies; linear antibodies; and multispecific antibodies formed from antibody fragments.

Preferably the immunoglobulin is a monoclonal antibody. The term "monoclonal antibody" as used herein refers to an antibody obtained from a population of substantially homogeneous antibodies, i.e. the individual antibodies comprising the population are identical except for possible naturally occurring mutations that may be present in minor amounts. In contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The immunoglobulin may be of the murine class IgG1, IgG2a, IgG2b, IgM, IgA, IgD or IgE, the human classes IgG1, IgG2, IgG3, IgG4, IgM, IgA1, IgA2, IgD or IgE, or combinations or fragments thereof.

The immunoglobulin may recognize any one or a combination of proteins including, but not limited to the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, CD152, IL-1a, IL-1ß, IL-1, IL-2, IL-3, IL-7, IL-4, IL-5, IL-8, IL-10, IL-12, IL-23, IL-2 receptor, IL-4 receptor, IL-6 receptor, IL-12 receptor, IL-13 receptor, IL-18 receptor subunits, PDGF-β, and analogues thereof, PLGF, VEGF, TGF, TGF-β2, TGF-p1, EGF receptor, PLGF receptor, VEGF receptor, platelet receptor gpIIb/IIIa, thrombopoeitin receptor, apoptosis receptor PD-1, hepatocyte growth factor, osteoprotegerin ligand, interferon gamma, B lymphocyte stimulator BLyS, T-cell activation regulator CTLA-4, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, α4β1 and α4β7 integrin, TRAIL receptors 1, 2, 3, and 4, RANK, a RANK ligand (RANKL), TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, sclerostin, MHC I, carcinoembryonic antigen (CEA), alpha-fetoprotein (AFP), tumour necrosis factor (TNF), Fc-y-1 receptor, HLA-DR 10 beta, HLA-DR antigen, L-selectin, and IFN-γ.

The immunoglobulin may be for example afelimomab, abciximab, adalimumab, alemtuzumab, arcitumomab, belimumab, canakinumab, cetuximab, denosumab, trastuzumab, imciromab, capromab, infliximab, ipilimumab, abciximab, rituximab, basiliximab, palivizumab, natalizumab, nivolumab, nofetumomab, omalizumab, daclizumab, ibritumomab, muromonab-CD3, edrecolomab, gemtuzumab, golimumab, certolizumab, eculizumab, ustekinumab, ocrelizumab, ofatumumab, obinutuzumab, panitumumab, pertuzumab, ranibizumab, romosozumab, tocilizumab, tositumomab, clenoliximab, keliximab, galiximab, foravirumab, lexatumumab, bevacizumab, and vedolizumab.

The immunoglobulin of the invention is preferably an IgG molecule, such as IgG1, IgG2, IgG3, or IgG4 molecule. More preferably, the immunoglobulin is IgG1. Even more preferably, the immunoglobulin is an IgG1 wherein at least the Fc part is human. The immunoglobulin may be a murine-human chimeric IgG1 wherein the Fc part of the IgG1 is human. Most preferably, the chimeric immunoglobulin is rituximab or infliximab.

Rituximab is a chimeric anti-cd20 antibody which is described in detail in, for example, WO9411026.

Infliximab is a chimeric anti-TNFα antibody which is described in detail in, for example, WO9216553.

The immunoglobulin may be a humanized IgG1 form a murine progenitor. Most preferably, the humanized antibody is trastuzumab or bevacizumab.

Trastuzumab is a humanized anti-HER2 antibody which is described in detail in, for example, WO9222653.

Bevacizumab is a humanized anti-VEGF antibody which is described in detail in, for example, WO9845331.

The immunoglobulin may be a fully human IgG1 antibody. Most preferably the human antibody is adalimumab or denosumab.

Adalimumab is a human anti-TNFα antibody which is described in detail in, for example, WO9729131.

Denosumab is a human anti-RANKL antibody which is described in detail in, for example, WO03002713.

In one embodiment the antibody may be rituximab or adalimumab.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity.

Furthermore, the monoclonal antibodies herein also include "humanized" antibodies. Such antibodies are obtained by "humanization" of non-human (for example murine) antibodies and contain only minimal sequences derived from the animal immunoglobulin. Most of the molecule is human sequence. Residues from a hypervariable region of the human recipient antibody are replaced by residues from a hypervariable region of a non-human donor antibody having the desired binding properties.

Finally, the monoclonal antibodies herein also include fully human antibodies which may be obtained by screening of a human antibody library.

In a preferred embodiment, the sample is derived from a cell culture supernatant which is obtained from recombinant CHO cell culture. Preferably, the sample is obtained from a recombinant cell culture in the growing phase.

The chromatography media may be disposable or reusable. In one embodiment the chromatography medium is reusable.

In a specific embodiment the anion exchange chromatography resin of step (a) is reusable.

Chromatography media that are reusable are cost-effective compared to chromatography media that are configured as disposables. In particular for the first pre-cleaning step large amounts of chromatography medium are used. Therefore, it is a particular advantage to use a reusable chromatography medium, e.g. a reusable anion exchange chromatography resin for the pre-cleaning step.

The term "reusable" as used herein means that the medium or resin is configured to be reused for more than one purification cycle, i.e. at least 2, 5, 10, 50, 100, 200, 300, 400, 500 or more purification cycles. Between each cycle the chromatography medium or resin may be washed and/or regenerated and/or stored.

In another specific embodiment, the chromatography medium of all chromatography steps is reusable.

By the terms "matrix" or "solid phase" is meant a non-aqueous matrix to which the ligand can adhere. The matrix of interest herein is generally one which comprises glass, ceramic, silica, cellulose, agarose, methacrylate polymer or polystyrene.

By "ligand" is meant any functional group which interacts with the protein or with at least one contaminant and which is covalently bound to the "matrix".

"Resin" means any chromatographic material in form of beads comprising a matrix with a bound functional group (ligand) which may interact with the protein or at least one contaminant. An exception are gel chromatography resins for size exclusion chromatography which are typically without any attached ligand. Resins may be supplied as beads of different sizes and packed in columns. Alternatively, pre-packed columns may be purchased.

The method of the invention may be used for immunoglobulin purification on a small and large scale. Preferably the method is carried out on a large scale.

"Small scale", also denoted as "laboratory scale", refers to purification of samples containing less than 50 g immunoglobulin, less than 10 g immunoglobulin, or less than 1 g immunoglobulin. "Small scale" also refers to purification processes in which the protein eluted from the column of the capture step amounts to less than 50 g immunoglobulin, less than 10 g immunoglobulin, or less than 1 g immunoglobulin.

"Large scale", also called as "production scale" or "manufacturing scale", refers to purification of samples containing more than 50 g immunoglobulin, more than 100 g immunoglobulin, more than 200 g immunoglobulin or over 300 g immunoglobulin. "Large scale" also refers to purification processes in which the protein eluted from the column of the capture step amounts to more than 50 g immunoglobulin, more than 100 g immunoglobulin, more than 200 g immunoglobulin or more than 300 g immunoglobulin.

EXAMPLES

The methods of the invention for purifying immunoglobulins are supported and illustrated by reference to the following examples. It has to be emphasized that these examples should by no means be construed as limiting the scope of the invention.

Example 1

Immunoglobulins and Cell Culture

The methods of the invention neither depend on specific antibodies nor on specific host cells used for the expression of the immunoglobulins. The same is true for the mode of expression and the selected culture conditions, which were optimized for maximum yields in the harvest. Different monoclonal antibodies were used during the development of the methods of the invention. They were successfully purified in various scales according to the methods of the invention. Most of the selected experiments presented in the Tables were performed with Rituximab, a mouse-human chimeric, anti-CD20, IgG1 antibody. In addition, some other experiments were performed with Adalimumab, a fully human, anti-TNFα, IgG1 antibody. Both antibodies were recombinantly expressed in CHO cells, which were propagated in fed-batch cultures of different scales. The experiments in the development phase were mainly performed with harvested culture fluid from a laboratory scale of 100 L. The production scale and maximum culture volume used in the examples was 1000 L. Unless specified otherwise, the scale always refers to the culture volume.

Example 2

Harvest of Cell Culture Fluid and Pre-Cleaning Filtration Steps

The following method is described for the 1000 L scale. Cells and cell debris were removed by separation using an LAPX404 separator (Alfa Laval) at 9600 rpm with a flow rate of 100 L/h. The separated culture fluid was serially filtered through the following filters (Pall Corporation): (i) Filter Capsule SXLP700416SP, (ii) Filter Capsule SXLPDE2408SP, and (iii) again Filter Capsule SXLPDE2408SP. Both depth filtration and microfiltration principles are achieved by this filter configuration. Prior to the first chromatography, the filtered culture fluid was additionally subjected to microfiltration using a Sartopore 2/0.2 μm membrane filter device (Sartorius).

Example 3

Selection of Chromatography Resins (Table 1 and Table 2)

A relatively large collection of common and potentially useful process chromatography resins from different suppliers were tested for their efficiency in a wide screening programme as pre-cleaning step, capture step, and polishing step (see FIGS. 2A and 2C). This was performed during the early stage of development of this invention. The resins were packed in small columns (10-20 ml) and the samples comprising Rituximab were taken from the 100 L laboratory scale, either directly after separation and filtration (pre-cleaning and capture steps) or from a Protein A eluate (polishing steps in binding mode). A cation exchange chromatography pool obtained after a Protein A and pre-cleaning chromatography was used for the polishing steps in flow-through mode. The chromatographic runs were performed with an Äkta Purifier System (GE Healthcare).

Pre-Cleaning Resins:

Eight different anion exchange chromatography resins were tested and compared in a flow-through mode. The resins were Capto Q, Q-Sepharose FF, Unosphere Q, Nuvia Q, Fractogel TMAE, Poros HQ, Q HyperCel, and Toyopearl Super Q 650. Packed columns were equilibrated with 10 mM Tris-HCl, pH 8.0. The test criteria were (i) maximum capacity in terms of passed sample volume until breakthrough of contaminants, (ii) regeneration (including discolouring), and (iii) the extent of precipitation after an acidification of the collected flow-through below pH 5.0. Four resins were found most suitable for use in a pre-cleaning step (Table 1) and except Nuvia Q they produced similar results. Nuvia Q, however, clearly proved superior and is the preferred resin (Table 2).

Affinity Capture Chromatography Resins with Protein A:

A total of nine different Protein A resins were tested and compared in the bind and elute mode without applying a washing step. The same conditions as regards column size, flow rate, and residence time were used. The column equilibration buffer was 40 mM Na-phosphate, 150 mM NaCl, pH 7.4. Elution was performed with 100 mM Na-citrate, pH 3.5. The tested resins were MabSelect, MabSelect Xtra, MabSelect SuRe, MabSelect SuRe LX, Unosphere Supra, ProSep Ultra Plus, Protein A Ceramic HyperD F, Poros MabCapture A, and Toyopearl rProtein A. The criteria were (i) dynamic and specific binding capacity (breakthrough determination), (ii) required regeneration procedure, (iii) sensitivity to harsh cleaning (NaOH, urea, Gu-HCl), (iv) purity of the eluate (residual HCP, leached Protein A), and (iv) cost calculation. Taken together, three resins were found to be superior and most useful (Table 1). Poros MabCapture A, and the two MabSelect SuRe resins from GE Healthcare were the most promising resin candidates for a large scale process. Mab-Capture A had a 15% lower HCP removal capacity compared to MabSelect SuRe and is second choice. The most preferred resin is MabSelect SuRe LX which had a somewhat higher binding capacity than MabSelect SuRe (Table 2).

Non-Affinity Capture Chromatography Resins:

A total of five different resins were tested in this category. The resins were Capto MMC (Mixed Mode), Capto S (cation exchanger), MEP HyperCel (Mixed Mode), PPA HyperCel (Mixed Mode), and Toyopearl AF Red (dye ligand based on Procion Red HE-3B). The criteria were (i) dynamic and specific binding capacity (breakthrough determination), (ii) required elution criteria, (iii) regeneration procedure (0.5M NaOH), and (iv) purity of the eluate (HCP). All these resins (Table 1) showed efficient capture abilities but different purification power. HCP in the eluate was qualitatively and quantitatively different. The non-affinity capture step can be applied prior to a subsequent Protein A affinity chromatography (see FIG. 2B) and then in principle functions as a second pre-cleaning step to further unburden the valuable Protein A column. However, two Mixed Mode resins turned out to be superior and can also be used as a capture step within a downstream sequence which is devoid of any Protein A affinity step (see FIG. 2C). These promising resins were Capto MMC and MEP HyperCel (Table 2).

Resins for Polishing Chromatography in Binding Mode:

With the exception of one Mixed Mode chromatography resin only cation exchangers were considered for this category. A large number (n=14) of common cation exchangers were tested: Poros HS, Poros XS, SP Sepharose HP, Capto SP Impres, YMC BioPro 30S, YMC BioPro 70S, Unosphere Rapid S, Unosphere Rapid S40, Nuvia S, Nuvia HR-S, Toyopearl SP 650S, Toyopearl GigaCap S 650S, Millipore ProRes S, and Fractogel EMD $SO_3$. The columns were loaded with Protein A (MabSelect SuRe) eluate, comprising Rituximab and low amounts of contaminants, adjusted to 10 mg/ml protein concentration with equilibration buffer. Not all resins were tested to the same extent. Besides the dynamic and specific binding capacities (breakthrough determination) also the ability to separate residual HCP and product-related impurities (aggregates, undesired charge variants) was investigated. The elution was performed with increasing salt and/or pH gradients. The resins showed significant differences as regards the separation of the impurities in the acid (charge variants) and basic (aggregates) fractions. This criterion was weighted because it is the intended purpose of an immunoglobulin polishing step. A total of six resins were found to be suitable for a polishing step (Table 1). Among Poros 50 HS, SP Sepharose HP, Capto SP Impres, Nuvia HR-S, Toyopearl SP 650S, and Fractogel EMD SO3 the cation exchanger from Applied Biosystems, Poros HS 50, and one resin from Bio-Rad, Nuvia HR-S, displayed the best removal potential for the contaminants HCP, aggregates, undesired charge variants, and leached Protein A. Additionally, CaptoAdhere, a positively charged Mixed Mode resin from GE Healthcare, was investigated for its usefulness as polishing step in the binding mode. The same sample, column size and criteria were applied in the same ways as for the cation exchangers. The equilibration buffer was 20 mM Na-phosphate, pH 8.2 and the pH of the sample was adjusted to 8.2 with NaOH and further diluted with equilibration buffer. Although the resin is capable of binding higher amounts a load of 20-23 mg/ml of Rituximab is required for efficient separation. Elution of bound protein was performed with 20 mM Na-phosphate, pH 6.0. The CaptoAdhere resin in the binding mode showed very promising removal power for contaminants and was selected as a preferred resin for a polishing step (Table 2).

Resins for Polishing Chromatography in Non-Binding Mode:

In this category only anion exchangers and one Mixed Mode resin were considered. A total of seven different common anion exchangers were tested: Poros HQ, Capto Q, Unosphere Q, Nuvia Q, Toyopearl GigaCap Q 650, Q HyperCel, and Fractogel EMD TMAE. The criteria were: maximum purity of Rituximab in the obtained flow-through with special focus on residual aggregates, HCDNA and HCP. The columns were loaded with a cation exchanger (Poros HS) pool after a Protein A (MabSelect SuRe) step. Three anion exchange chromatography resins, Poros HQ, Capto Q, and Nuvia Q were found most suitable for use in a polishing step in flow-through mode (Table 1). Additionally, CaptoAdhere, a positively charged Mixed Mode resin from GE Healthcare, was investigated for its usefulness for a polishing step in the flow-through mode. The same sample, column size and criteria were applied in the same way as for the anion exchangers. The equilibration buffer was 20 mM Na-phosphate, 100 mM NaCl, pH 7.8. The CaptoAdhere resin showed a remarkable removal power for contaminants also in the flow-through mode and was slightly superior to the anion exchange chromatography resins. This is readily explained by the additional hydrophobic interaction which supplements the anion exchange function. Thus, CaptoAdhere was selected as a preferred resin for a polishing step in flow-through mode (Table 2).

TABLE 1

Suitable process resins for use as pre-cleaning, capture and polishing chromatography step(s) [AEX = anion exchange chromatography; CEX = cation exchange chromatography; MMC = Mixed Mode chromatography]:

| Type and Mode | Resin | Supplier | Suitability |
|---|---|---|---|
| Pre-Cleaning Step AEX flow-through | Poros HQ | Applied Biosystems | + |
| | Fractogel TMAE | EMD Millipore | + |
| | Capto Q | GE Healthcare | + |
| | Nuvia Q | Bio-Rad | ++ |
| Protein A Affinity Capture Step | Poros MabCapture | Applied Biosystems | + |
| | MabSelect SuRe | GE Healthcare | ++ |
| | MabSelect SuRe LX | GE Healthcare | ++ |
| Non-Affinity Capture Step | Toyopearl AF Red | Tosoh Biosciences | + |
| | PPA Hypercel | Pall Corporation | + |
| | MEP Hypercel | Pall Corporation | ++ |
| | Capto MMC | GE Healthcare | ++ |
| | Capto S | GE Healthcare | + |
| Polishing Step Binding Mode (CEX or MMC) | Capto SP ImpRes | GE Healthcare | + |
| | Fractogel EMD SO3 | EMD Millipore | + |
| | Toyopearl SP 650S | Tosoh Biosciences | + |
| | Sepharose SP HR | GE Healthcare | + |
| | Nuvia HR-S | Bio-Rad | ++ |
| | Poros 50 HS | Applied Biosystems | ++ |
| | CaptoAdhere | GE Healthcare | ++ |
| Polishing Step Flow-through (AEX or MMC) | Poros 50 HQ | Applied Biosystems | + |
| | Capto Q | GE Healthcare | + |
| | CaptoAdhere | GE Healthcare | ++ |
| | Nuvia Q | Bio-Rad | + |

+ = suitable resin;
++ = preferred resin

TABLE 2

Preferred Chromatography Resins [AEX = anion exchange chromatography; CEX = cation exchange chromatography; MMC = Mixed Mode chromatography]:

| Process Step | Resin | Type | Ligand | Supplier |
|---|---|---|---|---|
| Pre-Cleaning | Nuvia Q | AEX | Trimethylammonium | Bio-Rad |
| Capture | MabSelect SuRe LX | Affinity | Alkali-stabilized Protein A derivative | GE Healthcare |
| Capture | MEP HyperCel | MMC | 4-Mercapto-ethyl-pyridine | Pall Corporation |
| Capture | Capto MMC | MMC | Multi modal weak cation exchanger | GE Healthcare |
| Polishing | Poros 50 HS | CEX | Sulfopropyl | Applied Biosystems |
| Polishing | Nuvia HR-S | CEX | Sulfonate | Bio-Rad |
| Polishing | CaptoAdhere | MMC | N-Benzyl-N-methyl ethanol amine | GE Healthcare |

Example 4

Pre-Cleaning Anion Exchange Chromatography Step

A 100 L scale (Rituximab or Adalimumab) and a 1000 L scale (Rituximab) was purified over the downstream sequences shown in FIGS. 2A-C. The preferred resin for the pre-cleaning chromatography step is Nuvia Q performed in the flow-through mode. This process step was performed with culture fluids obtained after the pre-cleaning filtration procedures described in Example 2. The pre-cleaning chromatography was performed in the flow-through mode with Nuvia Q anion exchange chromatography resin in order to reduce the impurity load (HCP, HCDNA, aggregates, lipids, pigments, etc.) for the subsequent capture step. The column packed with the resin (dimension for the 1000 L scale=60 cm diameter×16 cm height, packed volume about 45 L; dimension for the 100 L scale=14 cm diameter×27 cm height, packed volume about 4.1 L) was equilibrated consecutively with WFI (2 CV), 1M Tris-acetic acid pH 6.0 (3 CV) and 20 mM Tris-acetic acid pH 7.2 (4 CV). The product solution was passed through the column (17 g/L resin) followed by WFI (2 CV) with a flow rate of about 200 cm/h. The regeneration of the Nuvia Q resin was performed by washing in reverse direction consecutively with (i) 40 mM $NaH_2PO_4$, 10 mM EDTA, 2M urea, 1.5M NaCl, pH 7.2 (4 CV), (ii) 100 mM citric acid, 2M NaCl (10 CV), (iii) WFI (4 CV), (iv) 1M NaOH (4 CV), and (v) 10 mM NaOH (2 CV). The column was afterwards stored in 10 mM NaOH solution.

Example 5

Effect of the Pre-Cleaning Anion Exchange Chromatography Step on the Re-Use of MEP HyperCel Used as Capture Resin (Table 3)

MEP HyperCel is a preferred non-affinity resin for a capture step which can be applied in a large scale process with (FIG. 2B) or without (FIG. 2C) a subsequent Protein A affinity step. The contamination (fouling) of the MEP HyperCel column was found to be a severe disadvantage. However, this can be prevented or strongly reduced by applying a pre-cleaning anion exchange column, which was Nuvia Q in this example. Without a Nuvia Q pre-column the re-use of MEP HyperCel requires rigorous, long-lasting and expensive regeneration procedures and even then the lifetime is limited. The experiments of Table 2 are performed with small model columns (20 ml) packed with Nuvia Q and MEP HyperCel, respectively. The sample load and performance of the Nuvia Q chromatography was as described in Example 4. The flow-through was immediately loaded onto the MEP HyperCel without adjustments. In parallel a second capture column was directly loaded, i.e. by-passing the Nuvia Q step, with culture fluid according Example 2. The capture column was loaded until the maximum capacity was reached and product appeared in the flow-through (breakthrough). The bound IgG was eluted from the MEP HyperCel column by pH decrease (pH 4). The binding capacity was calculated from the volume until breakthrough. The Mixed Mode resin was simply regenerated, and re-equilibrated for the next run. The regeneration of MEP Hypercel was performed in reverse flow by passing a 100 mM citric acid solution, followed by 1M NaOH. The contact time with NaOH was 60 min after which the column was prepared for the next use by re-equilibration and complete removal of NaOH (pH control). The Nuvia Q column was regenerated as described in Example 4. A total of eight cycles were performed (seven re-uses). The results were summarized in Table 3 and support the superiority of the Nuvia Q step. There were no changes in the binding capacity when Nuvia Q pre-cleaning was applied. In contrast, without such a step, there was a decrease in the binding capacity from run to run which sank to 64% after eight cycles.

TABLE 3

Effect of an anion exchange chromatography (AEX) in flow-through mode as a pre-cleaning step on the re-use of the Mixed Mode resin MEP HyperCel used as capture step (IgG binding capacity per ml resin):

| Cycle Number | MEP HyperCel | AEX →MEP HyperCel |
|---|---|---|
| 1 | 16.5 mg/ml | 16.1 mg/ml |
| 2 | 13.2 mg/ml | 16.0 mg/ml |
| 3 | 12.6 mg/ml | 15.9 mg/ml |
| 4 | 11.9 mg/ml | 16.2 mg/ml |
| 5 | 11.5 mg/ml | 16.1 mg/ml |
| 6 | 11.0 mg/ml | 15.9 mg/ml |
| 7 | 10.7 mg/ml | 16.0 mg/ml |
| 8 | 10.5 mg/ml | 15.9 mg/ml |

Example 6

Capto MMC Capture Chromatography

The Capto MMC resin is a negatively charged Mixed Mode chromatography media (see Table 2) and was applied within the downstream sequence shown in the process flow schemes of FIG. 2B (five column process) and FIG. 2C (four column process). In these sequences, the Capto MMC functions in principle as a second pre-cleaning step to purify the sample and to get rid of critical contaminants, such as proteases, which can harm the subsequent Protein A affinity chromatography resin. In addition, this step allows a significant sample concentration and thus reduces the process time of the Protein A chromatography. The Capto MMC chromatography was performed in the binding mode and loaded with the Nuvia Q flow-through described in Example 4, which was adjusted to pH 5 with acetic acid. Both 100 L and 1000 L scales of Rituximab were purified according this method. The column dimension for the 1000 L scale was 60 cm diameter×15 cm height (packed volume about 42 L) and for the 100 L scale 20×14 cm (packed volume about 4.4 L). The resin was equilibrated with 20 mM Na-acetate, pH 5.0 and the column with the bound Rituximab was washed with 40 mM Na-phosphate, pH 6.5. The elution was optimized for maximum recovery and performed with 40 mM Na-phosphate, 250 mM NaCl, pH 7.5. The flow rates were 150-200 cm/h. The eluate was loaded directly onto the Protein A column.

Example 7

Protein A Capture Chromatography

The Protein A capture chromatography was performed with MabSelect SuRe (100 L scale) or MabSelect SuRe LX (1000 L). Except for the scales of the columns, the processing parameters were the same. The sample was taken either after the methods applied in Example 4 (process of FIG. 2A, Nuvia Q flow-through) or after the methods applied in Example 6 (process of FIG. 2B, Capto MMC eluate). The column dimension for the 1000 L scale was 40 cm diameter× 30 cm height (packed volume about 38 L) and for the 100 L scale 20×10.4 cm (packed volume about 3.2 L). The Protein A column was equilibrated with 40 mM Na-phosphate, 150 mM NaCl, pH 7.4. Unless specified otherwise, the product solution was loaded with 20 g protein/L resin (100 L scale) or 35 g protein/L resin (1000 L scale). The column was washed with equilibration buffer (2 CV), followed by 40 mM Na-phosphate, 1.5M NaCl, 2M urea, 10 mM EDTA, pH 7.4. The elution was performed with 100 mM Na-citrate, pH 3.5. The flow rates were 140 cm/h. The regeneration of the Mabselect SuRe or MabSelect SuRe LX resin was performed by washing in reverse direction consecutively with (i) 0.2M NaOH (2 CV), (ii) WFI (2 CV), 3.5% acetic acid, 100 mM Na-sulphate (2 CV) and (iii) WFI (2 CV). The column was re-equilibrated for the next run or stored in 20% ethanol.

Example 8

Effect of the Pre-Cleaning Anion Exchange Chromatography on Leached Protein A (Table 4)

To investigate the effect of a pre-cleaning chromatography (Nuvia Q) and the temperature on the leaching of Protein A (MabSelect SuRe LX), a series of experiments was performed in a downscaled Protein A affinity chromatography. The columns used had a volume of 12 ml. An Äkta Purifier System (GE Healthcare) was applied for the chromatographic runs. The samples were small aliquots taken from a 1000 L batch of Rituximab. The samples were taken either from the process step obtained after the procedures described in Example 2 (prior to the Nuvia Q pre-cleaning step) or after the procedures described in Example 3 (after the Nuvia Q pre-cleaning step). The method of the Protein A affinity chromatography was performed according Example 7. The columns were loaded with 25-30 mg protein/ml resin. Sample and Protein A affinity chromatography were kept at room temperature (20-25° C.) or placed in a cooling chamber (2-8° C.). Two parallel samples were taken from two different aliquots respectively and purified and tested in parallel. The results are shown in Table 4. The mean values of the two parallel runs of leaching at room temperature without a preceding Nuvia Q step was 23.4 ng/mg (Protein A equivalent per mg IgG). The effect of the pre-cleaning step is evident (Table 4). At room temperature only 9.1 ng/mg (=39%) of the leaching occurred when the sample was passed through a Nuvia Q column prior to the Protein A step. At the low temperature, which itself had a significant effect on leaching, the effect is also seen. The leaching without Nuvia Q was 5.0 ng/mg and with Nuvia Q it was 3.4 ng/mg (68%) on average (Table 4). A Nuvia Q step significantly reduces the Protein A leaching and allows the more preferred room temperature for the affinity chromatography step to be used. The effect of Nuvia Q on Protein A leaching is best explained by the capture of proteolytic activities which bind to the Nuvia Q resin.

TABLE 4

Effect of the pre-cleaning anion exchange (Nuvia Q) chromatography step on leached Protein A (from MabSelect SuRe LX) measured in the Protein A eluate. Two parallel chromatographies were performed at two different temperatures:

| | | Protein A Leaching | |
|---|---|---|---|
| Temperature | Sample | No pre-cleaning | With pre-cleaning |
| Room temp. | 1 | 25.1 ng/mg | 10.3 ng/mg |
| (20-25° C.) | 2 | 21.6 ng/mg | 7.8 ng/mg |
| Cooled | 3 | 4.9 ng/mg | 3.1 ng/mg |
| (2-8° C.) | 4 | 5.0 ng/mg | 3.6 ng/mg |

Example 9

Connected Pre-Cleaning and Capture Columns

Since the pre-cleaning anion exchange step with Nuvia Q was performed in flow-through and the subsequent Protein A affinity resin (MabSelect SuRe LX) is able to capture the immunoglobulin efficiently out of this flow-through, it was possible to directly connect the Nuvia Q column with the MabSelect SuRe LX column. The downstream processes summarized in FIGS. 2A and 2B were run from a 1000 L scale (Rituximab) with such connected pre-cleaning and capture columns. But also 100 L scale processes were performed with connected columns unless specified otherwise. The two columns were equilibrated separately and then connected by valve switching. The product solution was loaded with about 100 L/h (1000 L scale) or about 10 L/h (100 L scale) onto the connected columns in up-flow direction as described in Example 4 for Nuvia Q. After the wash with WFI (2 CV) the Nuvia Q column was by-passed by valve switching at the chromatography skid and regenerated in the reverse flow as described in Example 4. The further processing, i.e. washing, elution, and regeneration of the Protein A column was performed in the disconnected configuration as described in Example 7.

Example 10

Virus Inactivation

As shown in the FIGS. 1 and 2, a viral inactivation step takes place after the Protein A affinity chromatography. Advantage is taken of the low pH elution from the affinity matrix. In such an aqueous acid environment many viruses, especially those of the enveloped type, are instable and disintegrate. The Protein A method developed for this invention produces an eluate having a pH of 3.5 (see Example 7). Similarly, the eluate of the Mixed Mode capture column (MEP HyperCel or Capto MMC) has a low pH of 4 (see Examples 5 and 6). The inactivation for the MabSelect SuRe LX eluate (1000 L scale, Rituximab) is hereinafter described. The monoclonal antibody was eluted from the Protein A column in 100 mM Na-citrate buffer, pH 3.5 directly into the virus inactivation tank A. The eluate was diluted about 2-fold by WFI directly in the tank A. The pH of the solution was controlled and re-adjusted to 3.5 with 100 mM citric acid, if necessary, and the solution was subsequently transferred to the virus inactivation tank B, where it was agitated with 65 rpm at a temperature of 20-24° C. for 60 minutes. Then the pH of the solution was adjusted to pH 4.5 with 50 mM NaOH, providing the starting condition for the subsequent cation exchange chromatography step.

Example 11

Cation Exchange Chromatography with Poros 50 HS (Polishing 1)

Separation of contaminants and product-related substances such as charge variants was performed by cationic exchange chromatography being the first polishing step. This step was included in all purification sequences (100 L Rituximab and Adalimumab, 1000 L Rituximab). The packed column with Poros 50 HS resin (dimension for the 1000 L scale=60 cm diameter×32 cm height, packed volume about 90 L; dimension for the 100 L scale=25 cm diameter× 15 cm height, packed volume about 7.3 L) was equilibrated consecutively by (i) WFI (water for injection, 2 CV) and (ii) 20 mM Na-citrate, pH 5.5 (4 CV). The product solution obtained after the virus inactivation and the sample adjustments (pH 4.5) as described in Example 10 was loaded onto the column with about 8 g protein/L resin, thereby passing a 0.45 µm Kleenpak Nova pre-filter (Pall Corporation). The column was washed with WFI (1 CV) before a gradient elution followed. The gradient was formed by mixing 20 mM Na-citrate, pH 5.5 (buffer A) and 40 mM Na-phosphate, pH 7.8 (buffer B) in the following ratios and sequence: (i) 100% A (0.2 CV), (ii) linear gradient to 40% A+60% B (2 CV); (iii) linear gradient to 100% B (6 CV); (iv) 100% B (2 CV). The flow rates were 150 cm/h. The eluate was separated in fractions to allow specific pooling. The regeneration of the Poros 50 HS resin was performed by washing consecutively with (i) 2M NaCl (1 CV) and (ii) 1M NaOH (2 CV). The column was afterwards stored in 10 mM NaOH.

Example 12

Mixed Mode Chromatography with CaptoAdhere (Polishing 2)

The second polishing step is optional and was applied for 100 L and 1000 L scales of Rituximab. The selected resin for the final chromatography in the processes with two polishing steps (FIGS. 2A and 2B) was CaptoAdhere, which makes use of the ligand N-benzyl-N-methyl ethanolamine. The ligand bears positively charged groups and therefore provides beside hydrophobic interactions also anion exchanger functions. The chromatography is able to further reduce the remaining traces of contaminants, such as HCDNA and HCP. Residual leached Protein A, product aggregates and product fragments can also be removed by this step. The CaptoAdhere polishing step was performed in flow-through mode as well as in binding mode.

CaptoAdhere Chromatography in Flow-Through Mode:

The sample for this final chromatography was the Poros 50 HS pool subsequent to the procedures described in Example 11. The size of the packed column for the 1000 L scale was 14 cm diameter×13 cm height (packed volume about 2 L) and for the 100 L scale 5×13 cm (packed volume about 0.2 L). The column was equilibrated with 20 mM Na-phosphate, 100 mM NaCl, pH 7.8. The pH of the pooled fractions was adjusted to 7.8 with 0.2M NaOH and the conductivity was raised to 10-12 mS/cm with 1M NaCl. The adjusted pool was passed through the CaptoAdhere column with a load of 250-275 g protein/L resin and the entire flow-through was collected. The flow rates were 300 cm/h. The regeneration of the CaptoAdhere resin was performed by washing consecutively with (i) 100 mM citric acid, 2M NaCl (2 CV), (ii) 2M NaCl (1 CV), (iii) 1M NaOH (2 CV), and (iv) 10 mM NaOH (2 CV). The column was afterwards stored in 10 mM NaOH.

CaptoAdhere Chromatography in Binding Mode:

The pH and conductivity of the Poros 50 HS pool obtained subsequent to the procedures described in Example 11 was adjusted to pH 8.2 and 3.2 mS/cm, respectively. The size of the packed column for the 1000 L scale was 40 cm diameter×28 cm height (packed volume about 35 L) and for the 100 L scale 14×27 cm (packed volume about 4.1 L). The resin was equilibrated with 20 mM Na-phosphate, pH 8.2. The product solution was loaded onto the column with 15-20 g protein/L resin). The elution was performed with 20 mM Na-phosphate, pH 6.0. The flow rates were 300 cm/h. The column was regenerated as described for the method of the flow-through mode.

Example 13

Final Filtration Steps

Between the last chromatography and the filling of the final bulk of drug substance, there are several filtration steps required to formulate into the selected storage buffer, to fix the desired concentrations and to remove viruses. The purification methods of the invention for immunoglobulins do not depend on these filtration methods. Therefore, the methods, equipment and selected membranes in this example have to be understood as just one option and discretionary changes are possible. The methods for the 1000 L scale for a process with two polishing steps are described briefly below.

Buffer Exchange by Tangential Flow Ultrafiltration/Diafiltration (UF/DF):

The eluate from the CaptoAdhere column was collected in the tank of the UF/DF skid and concentrated to 8 g/L using the Omega Centrasette membrane cassette (Pall Corporation, 30 kD cutoff). The retentate was diafiltered using 10 volumes of formulation buffer (25 mM Na-citrate, 154 mM NaCl, pH 6.5).

Virus Removal by Nanofiltration:

Nanofiltration is the most demanding and most reliable virus removal step operating on the basis of size exclusion in the nanometer range. The diafiltered product solution was transferred into a movable tank and then subjected to nanofiltration using a Viresolve Pro Modus 1.3 filter (Millipore, 20 nm pore size). The filter was conditioned with 25 mM Na-citrate, 154 mM NaCl, pH 6.5 prior to the filtration of the product solution. For the protection of the nanofilter a Sartopore 2 MidiCaps prefilter (Sartorius, 0.2 µm pore size) was applied. Filtration was performed by overpressure at a maximum of 2 bar.

Concentration and Final Formulation by Tangential Flow Ultrafiltration/Diafiltration (UF/DF):

The nanofiltered product solution was collected in the tank of the UF/DF skid and was concentrated to about 10.2 g/L using Omega Centrasette membrane cassette (Pall Corporation, 30 kD cutoff). The concentrated product solution was transferred to a movable tank. The tank was placed under a laminar airflow and Tween 80 was added to a final concentration of 0.09% (w/w).

Final Microfiltration (Sterile Filtration):

The final microfiltration was performed with a 0.2 µm Mini Kleenpak filter capsule (Pall Corporation).

Example 14

Final Purities of Batches Obtained by Different Processes (Table 5)

The results with respect to final purity of two representative batches produced by the conventional process of FIG. 2A (according e.g. Fahrner R L 2001) and the new process of FIG. 2B are summarized in Table 5. The immunoglobulin was Rituximab and purified from the 100 L scale. The process steps of the conventional method of purification (process 1B) consist of three chromatographies, (i) MabSelect SuRe (capture), (ii) Poros 50 HS (binding mode), and (iii) Poros 50 HQ (flow-through mode). The chromatography sequence of the new process (process 2B) consists of (i) Nuvia Q (pre-cleaning), (ii) Capto MMC (capture), (iii) MabSelect SuRe (intermediate), (iv) Poros 50 HS (binding mode, polishing 1), and (v) CaptoAdhere (flow-through mode, polishing 2). The individual steps were performed as described in the Examples 1, 2, 4, 6, 7, and 10-13. The selected purity parameters for Table 5 are (i) the relative amount of the IgG monomer (in %), (ii) residual host cell proteins (HCP, in ng/mg IgG) and (iii) residual host cell DNA (HCDNA, in pg/g IgG). The analytical methods are described in the Example 15 below. The batch purified according the new process 2B had a higher purity compared to the batch purified according the classical process 1B as seen with all three parameters (Table 5).

TABLE 5

Comparison of the quality of two purified batches obtained by two different processes, the conventional process (1B) and one of the invented processes (2B). "Process 1B" refers to the standard process without a pre-cleaning chromatography step as shown in FIG. 1B. "Process 2B" refers to the invented process shown in FIG. 2B including a pre-cleaning chromatography step (Nuvia Q flow-through) and a Mixed Mode chromatography capture step (Capto MMC) followed by Protein A (MabSelect SuRe). The test methods were: Size exclusion-high performance liquid chromatography (SEC-HPLC), enzyme-linked immunosorbent assay (ELISA), and quantitative polymerase chain reaction (qPCR). The test parameters were monomeric IgG in percent, host cell protein (HCP) per mg IgG, and host cell DNA (HCDNA) per g IgG.

| Test method | Parameter | Process 1B | Process 2B |
|---|---|---|---|
| SEC-HPLC | Monomer (%) | 99.6 | 99.7 |
| ELISA | HCP (ng/mg) | 4.3 | 1.1 |
| qPCR | HCDNA (pg/g) | 289 | 142 |

Example 15

Analytical Methods

Several analytical methods both during the process and at the end of the process were applied to characterise the quality of the purified immunoglobulins. These methods were standard methods and described in the literature e.g. the Eur. Pharm. The principles of those methods which produced the results for the Tables are briefly described below:

High Performance Size-Exclusion Chromatography (SEC-HPLC):

The SEC-HPLC method was applied for the determination of impurities with molecular masses differing from that of the immunoglobulin. Size-exclusion chromatography (SEC) is a technique based on separation of molecules on the basis of the hydrodynamic diameters that are proportional to their sizes. A high-performance liquid chromatography system for SEC (SE-HPLC) was used which had a much better resolution than conventional SEC. The chromatography was performed as described in the literature (e.g. WO2013067301) to quantify monomers, dimers, aggregates and fragments of the immunoglobulin. The detection of the proteins was based on UV absorption. Relative purity refers to the area of the integrated monomer peak in % of the total area of all peaks. The test results were calculated from the average of replicate measurements.

Enzyme-Linked Immunosorbent Assay (ELISA) for Quantifying Host Cell Proteins (HCP):

The measurement was performed by a sandwich ELISA method. The CHO host cell proteins are bound to specific anti-CHO antibodies immobilized onto the polystyrene surface of a standard 96-well microtest plate, followed by binding to a secondary antibody labelled with horseradish peroxidase (HRP). Afterwards the enzyme reaction was performed by adding 3,3',5,5' tetramethylbenzidine (TMB) substrate to the wells which, depending on the presence of antibody-peroxidase conjugate, results in a coloured product, detectable by VIS light absorbance. The microtest plate was read at 450 nm (with a reference wavelength of 620 nm).

Enzyme-Linked Immunosorbent Assay (ELISA) for Quantifying Leached Protein A:

The measurement was performed using the commercially available MabSelect Sure Ligand ELISA kit from Repligen. The leached MabSelect Sure ligands are bound to specific anti-Protein A rabbit antibodies immobilized onto the polystyrene surface of a standard 96-well microtest plate, followed by binding to a secondary antibody labelled with biotin. The presence of bound biotin was detected by incubating the wells with a streptavidin-horseradish peroxidase conjugate. Afterwards the enzyme reaction was performed by adding 3,3',5,5' tetramethylbenzidine (TMB) substrate to the wells which, depending on the presence of antibody-peroxidase conjugate, results in a coloured product, detectable by VIS light absorbance. The microtest plate was read at 450 nm (with a reference wavelength of 620 nm). The assay sensitivity was 0.1 ng/ml sample.

Quantitative Polymerase Chain Reaction (qPCR) for Quanting Host Cell DNA (HCDNA):

The measurement was performed by a real-time quantitative PCR method based on the TaqMan chemistry (Applied Biosystems). The method is very sensitive and specific in detecting DNA contamination. The assay is based on sequence-specific amplification and real-time fluorescence detection of well-defined DNA fragments by polymerase chain reaction (PCR) using sequence-specific primers (SSP) and fluorescently labeled hybridization probes (TaqMan®). The whole method including instrumentation, reagents, sampling and software-based calculation was performed according to supplier's instructions. In the PCR reaction a large amount of double-stranded DNA is synthesized from the starting DNA region determined by a specific primer. The oligonucleotide probes which are labeled with the reporter and the quencher dye bind to the regions of the template DNA to be multiplied. During the PCR reaction the DNA polymerase decomposes the probe, so that the physical proximity of the two dyes ends and the reporter dye emits fluorescent light that is proportional to the synthesized product of the PCR reaction. CHO-specific probe and primers are used in the measurement, which multiply the amount of the appropriate regions of the CHO host cell DNA. During this step the fluorescent signal increases and after a certain number of cycles the fluorescence exceeds a threshold. This number of cycles is proportional to the starting amount of DNA. It is possible to determine the absolute amount of the host cell DNA in the samples by comparing the number of cycles obtained with the sample to a calibration curve.

Example 16

Validation of the Removal and Inactivation of Viruses

Viral removal and/or inactivation are required for the production process of a recombinant protein drug such as a monoclonal antibody produced by cell culture, because of concerns about contamination with viruses from raw materials or production steps. As a result, there is a considerable regulatory demand for the viral safety of every manufacturing process which results in a biological therapeutic protein derived from cell cultures. The downstream process has to be validated for its capacity to remove and/or inactivate potential viral contaminations in compliance with existing guidelines from the respective regulatory authorities, e.g. the European Medicine Agency (EMA) and the US Food And Drug Administration (FDA). The aim of the performed virus clearance study was to demonstrate the effective removal and inactivation of viruses during the manufacturing process, as part of the demonstration of the overall safety of recombinant protein drugs from cell culture sources.

Selection of the Process Steps:

The downstream process of the IgG1 antibody Rituximab was validated for selected steps. The analysed process steps were representative down-scaled versions of the corresponding large scale steps as described in the previous examples. Four process steps were selected:

a) Pre-cleaning anion exchange chromatography with Nuvia Q (see Example 4)
b) Virus inactivation of the Protein A eluate at low pH (see Example 10)
c) Cation exchange chromatography with Poros HS (see Example 11)
d) Nanofiltration with Viresolve Pro (see Example 13)

Selection of Viruses:

Two frequently used model viruses were selected:

a) Murine Leukemia Virus (MuLV)
b) Minute Virus of Mice (MVM)

MuLV is a member of the Retroviridae, which are single-stranded RNA viruses with an envelope and a size of about 80-100 nm. MVM is a member of the Parvoviridae, which are non-enveloped, single-stranded DNA viruses. Parvoviruses belong to the smallest viruses known, with sizes of 20-24 nm. Both viruses are obtained from the American Type Culture Collection (ATCC).

Performance of the Experiments:

Authentic intermediate process samples from one large scale batch were stored frozen ($\leq -15°$ C.). Aliquots of 20 ml were thawed prior to the experiments and were spiked with high virus titers of MuLV or MVM, respectively. The process step b) "Virus inactivation of the Protein A eluate at low pH" (see Example 10) was tested only for MuLV. Due to the morphology of the naked virus capsids Parvoviruses are known for their resistance to low pH treatment. Therefore, MVM was not tested for the low pH incubation. The spiked starting materials and the processed samples were quantitatively analysed using virus-specific cell-based infectivity assays and qPCR and the reduction factors were calculated as $\log_{10}$ values. All test materials were pre-investigated for interference with the assays and parallel control incubations prove the stability of the viruses during the duration of the experiments. The infectivity assays only detect infectious viruses, whereas the qPCR comprises both, infectious and inactivated viruses. For every process step and virus type duplicate runs were performed. In case the processed sample contained no detectable virus titer, the calculated detection limit of the assay was used as maximum titer. The reduction factors were then expressed as at least $\log_{10}$ "$\geq$".

Results of the Virus Clearance Study:

The results of the individual experiments were shown for each run, step, and virus in Table 6. The high reduction factors of the pre-cleaning step based on a simple anion exchange chromatography in flow through mode (resin Nuvia Q) was surprising. $\log_{10}$ reduction factors of at least 6.5 to 6.7 for MuLV and 6.6 for MVM were found. This step was the most superior one among the four tested. Especially in case of the difficult Parvovirus MVM this was not expected. Moreover, by using the combination of pre-cleaning anion exchange chromatography and a simple 60 min hold step for the Protein A eluate (pH 3.5) a cumulative reduction factor of at least 12.3 could be obtained for enveloped viruses such as MuLV. The total cumulative $\log_{10}$ reduction factors were 21.7 for MuLV and four steps and at least 13.3 for MVM and three steps.

TABLE 6

Log$_{10}$ reduction factors of different process steps for the reduction of two model viruses, Murine Leukemia Virus (MuLV) and Minute Virus of Mice (MVM). Two runs were performed per step and virus.

| Process Step | MuLV Run 1/Run 2 | MVM Run 1/Run 2 |
|---|---|---|
| Pre-Cleaning AEX (Nuvia Q) | ≥6.74/≥6.51 | 6.57/6.63 |
| Protein A eluate hold step (pH 3.5) | 6.30/5.81 | Not done |
| Polishing CEX (Poros HS) | 5.55/5.06 | 1.57/1.33 |
| Nanofiltration (Viresolve Pro) | ≥4.53/≥4.35 | ≥5.53/≥5.41 |
| Cumulative Reduction | ≥21.7-≥23.1 | ≥13.3-13.7 |

LIST OF REFERENCES

1. F. Bulens et al., 1991 "Construction and characterization of a functional chimeric murine—human antibody directed against human fibrin fragment-D dimer", Eur. J. Biochem. 195, 235-242
2. R. L. Fahrner et al., 2001 "Industrial Purification of Pharmaceutical Antibodies: Development, Operation, and Validation of Chromatography Processes", Biotechnology and Genetic Engineering Reviews 18, 301-327
3. S. S. Farid, 2009 "Economic Drivers and Trade-Offs in Antibody Purification Processes: The future of therapeutic MAbs lies in the development of economically feasible downstream processes", BioPharm Int. Supplements, Oct. 2, 2009
4. P. Füglistaller, 1989 "Comparison of immunoglobulin binding capacities and ligand leakage using eight different protein A affinity chromatography matrices", J. Immunol. Meth. 124, 171-177
5. P. Gagnon, 1996 "Purification Tools for Monoclonal Antibodies", Validated Biosystems, Inc., 1-253
6. B. Kelly et al., 2009, "Downstream processing of monoclonal antibodies: Current practices and future opportunities", in: Process Scale Purification of Antibodies, edited by U. Gottschalk, John Wiley & Sons, Inc.
7. H. F. Liu, 2010 "Recovery and purification process development for monoclonal antibody production", mabs Landes Biosciences 2(5), 480-499
8. A.-M. VanDamme et al., 1990, "Construction and characterization of a recombinant murine monoclonal antibody directed against human fibrin fragment-D dimer", Eur. J. Biochem. 192, 767-775
9. Y. Yigsaw et al., 2006 "Exploitation of the Adsorptive Properties of Depth Filters for Host Cell Protein Removal during Monoclonal Antibody Purification", Biotechnol. Prog. 22, 288-296
10. EP0345549
11. EP0550400
12. WO03002713
13. WO03041859
14. WO03102132
15. WO2001150110
16. WO2004076485
17. WO2005016968
18. WO2009058812
19. WO2009138484
20. WO2010141039
21. WO2011017514
22. WO2011049798
23. WO2011090720
24. WO2011150110
25. WO2013066707
26. WO2013067301
27. WO9216553
28. WO9222653
29. WO9411026
30. WO9522389
31. WO9729131
32. WO9845331
33. EMA Committee for proprietary medical products (CPMP) 14 Feb. 1996, "Note for guidance on virus validation studies: the design, contribution and interpretation of studies validating the inactivation and removal of viruses"; CPMP/BWP/268/95 Appendix II

The invention claimed is:

1. A method for purifying an immunoglobulin from a sample comprising the immunoglobulin and at least one impurity on a large scale, the method comprising the following steps in the following order:
    (a) exposing the sample to anion exchange chromatography and obtaining the immunoglobulin, which is not bound to the anion exchange chromatography resin, in the flow-through;
    (b) exposing the flow-through obtained in step (a) either to Protein A affinity chromatography, wherein the immunoglobulin is bound to the Protein A affinity chromatography resin, and obtaining the immunoglobulin in the eluate by eluting the protein from the Protein A affinity chromatography resin, or to Mixed Mode chromatography, wherein the immunoglobulin is bound to the Mixed Mode chromatography resin, and obtaining the immunoglobulin in the eluate by eluting the protein from the Mixed Mode chromatography resin;
    (c) incubating the eluate obtained in step (b) at low pH of 2.5 to 4.5 for a defined time;
    wherein the method results in a cumulative log$_{10}$ reduction factor for steps (a) and (c) of at least 10 with respect to enveloped viruses,
    wherein the sample is harvested cell culture fluid, cell culture supernatant or pretreated cell culture supernatant.

2. The method of claim 1, further comprising the following step:
    (d) exposing the eluate after the incubation of step (c), or a composition derived therefrom and obtained after one or more further processing steps performed after step (c), to nanofiltration;
    wherein the method results in a cumulative log$_{10}$ reduction factor for steps (a) and (d) of at least 10 with respect to non-enveloped viruses and/or wherein the method results in a cumulative log$_{10}$ reduction factor of steps (a), (c) and (d) of at least 15 with respect to enveloped viruses.

3. The method of claim 2, further comprising the following step:
    (c2) exposing the eluate obtained in step (c), or a composition derived therefrom and obtained after one or more further processing steps performed after step (c), to cation exchange chromatography, wherein the immunoglobulin is bound to the cation exchange chromatography resin, and obtaining the immunoglobulin in the eluate by eluting the protein from the cation exchange chromatography resin;
    wherein the method results in a cumulative log$_{10}$ reduction factor for steps (a), (c) and (c2) of at least 15 with respect to enveloped viruses.

4. The method of claim 3, wherein the method results in a cumulative log$_{10}$ reduction factor for steps (a), (c), (c2) and (d) of at least 20 with respect to enveloped viruses and/or wherein the method results in a cumulative $\log_{10}$ reduction factor for steps (a), (c2) and (d) of at least 12 with respect to non-enveloped viruses.

5. The method of claim 1, wherein the anion exchange chromatography of step (a) is strong anion chromatography comprising a ligand which is a strong anion exchange chromatography ligand except trimethylammoniumethyl bound to a methacrylate polymeric matrix, wherein the ligand is selected from the group consisting of quaternary aminoethyl (QAE) moieties, quaternary ammonium moieties and trimethylammonium moieties, wherein the ligand is preferably trimethylammonium ($-N(CH_3)_3^+$).

* * * * *